(12) United States Patent
Peters Lauthier et al.

(10) Patent No.: US 10,673,133 B2
(45) Date of Patent: *Jun. 2, 2020

(54) CAPTURE AND REGENERATION OF SUBTLE ENERGY RESONANCE SIGNALS

(71) Applicant: Chi-Box, Inc., Bethesda, MD (US)

(72) Inventors: Lorie Peters Lauthier, Bethesda, MD (US); Norman Boyce, Ducktown, TN (US)

(73) Assignee: Chi-Box, Inc., Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/195,727

(22) Filed: Nov. 19, 2018

(65) Prior Publication Data

US 2019/0109376 A1 Apr. 11, 2019

Related U.S. Application Data

(63) Continuation-in-part of application No. 15/635,100, filed on Jun. 27, 2017, now Pat. No. 10,177,833.

(Continued)

(51) Int. Cl.
*H01Q 1/52* (2006.01)
*H04B 7/15* (2006.01)
(Continued)

(52) U.S. Cl.
CPC ............... *H01Q 1/526* (2013.01); *A61B 5/04* (2013.01); *A61B 5/6887* (2013.01); *A61N 1/00* (2013.01);
(Continued)

(58) Field of Classification Search
CPC .......... H01Q 1/526; H01Q 1/38; H01Q 1/521; H01Q 7/00; H04B 7/15; H04B 7/06;
(Continued)

(56) References Cited

U.S. PATENT DOCUMENTS

| 6,424,820 B1* | 7/2002 | Burdick | ............... H04B 5/0081 455/132 |
| 2007/0024520 A1* | 2/2007 | Preble | .................... H01Q 1/084 343/895 |

(Continued)

*Primary Examiner* — Syed Haider
(74) *Attorney, Agent, or Firm* — Carr & Ferrell LLP

(57) ABSTRACT

Systems and methods for capture, recording, and regeneration of subtle energy resonance signals are described herein. A system for capturing and recording the signals may include an antenna array disposed within an electromagnetic shield, a signal processor, and a memory coupled to at least one processor. The antenna array may include at least one antenna comprising a conductive disk and an amplifier circuit board, the antenna array detecting and receiving subtle energy resonance signals from a source. The signal processor converts the analog signals into digital signals, which are then stored into the memory. The electromagnetic shield houses the antenna array and minimizes electromagnetic interference with the received signal. Such a controlled environment ensures the purity of the recorded subtle energy resonance signals for regeneration. Regeneration is accomplished with a second antenna coupled to a digital regeneration device for short-range broadcasting, affecting manifestations of subtle energy resonance in a subject.

22 Claims, 15 Drawing Sheets

Related U.S. Application Data

(60) Provisional application No. 62/495,539, filed on Sep. 19, 2016.

(51) Int. Cl.
    *H01Q 1/38*         (2006.01)
    *H01Q 7/00*         (2006.01)
    *H04B 7/06*         (2006.01)
    *A61N 1/00*         (2006.01)
    *A61B 5/04*         (2006.01)
    *A61N 2/02*         (2006.01)
    *A61B 5/00*         (2006.01)

(52) U.S. Cl.
    CPC ................. *A61N 2/02* (2013.01); *H01Q 1/38* (2013.01); *H01Q 1/521* (2013.01); *H01Q 7/00* (2013.01); *H04B 7/06* (2013.01); *H04B 7/15* (2013.01); *A61M 2230/65* (2013.01)

(58) Field of Classification Search
    CPC .......... A61N 2/02; A61N 1/00; A61B 5/6887; A61B 5/04; A61M 2230/65
    See application file for complete search history.

(56) References Cited

U.S. PATENT DOCUMENTS

| | | | |
|---|---|---|---|
| 2008/0223931 A1* | 9/2008 | Spiess ................. | G06K 7/0008 235/439 |
| 2011/0131477 A1* | 6/2011 | Jungleib ............. | G06F 11/3037 714/819 |
| 2012/0034959 A1* | 2/2012 | Edeler ................... | H04M 1/035 455/575.5 |
| 2018/0277960 A1* | 9/2018 | Johnsson ............... | H01Q 1/243 |

\* cited by examiner

| Number on X axis | Program in Subtle Energy Resonance Playback System |
|---|---|
| 1 | Addiction/pain killers |
| 2 | Alleviating allergies |
| 3 | De-stress S101 |
| 4 | De-stress E201 |
| 5 | Alleviating Lyme |
| 6 | Universal drug addiction |
| 7 | Energizing |
| 8 | Burns |
| 9 | Liver detox |

US 10,673,133 B2

CAPTURE AND REGENERATION OF SUBTLE ENERGY RESONANCE SIGNALS

CROSS-REFERENCE TO RELATED APPLICATIONS

The present application is a continuation-in-part of U.S. patent application Ser. No. 15/635,100 filed on Jun. 27, 2017 and titled "Capture and Regeneration of Subtle Energy Resonance Signals," which claims the benefit of U.S. Provisional Application No. 62/495,539, entitled "Method and apparatus to record & playback subtle energy resonance," filed on Sep. 19, 2016, which is hereby incorporated by reference herein in its entirety.

FIELD OF THE INVENTION

The present disclosure relates generally to personal wellness devices and, more particularly, to the capture and regeneration of subtle energy resonance signals.

BACKGROUND OF THE INVENTION

Evidence for resonance between objects is widely understood and recognized throughout standard Newtonian mechanics and generally employed through standard Maxwell's electrodynamics. Physicists refer to this classical energetic model as the U(1) gauge state. Subtle energy resonance manifestation may arise from the application of ambient electromagnetic (EM) waves. From cell to bone, the human body is composed almost entirely from complex crystalline arrays built from carbon, calcium, sodium, potassium, and magnesium, with other trace mineral compounds. As a result, the state and growth of this biodynamic living crystalline structure may be influenced, guided, and imprinted by the exposure to an overlay of global and local EM systems. Such systems may include organic structures such as trees, plants, and flowers, and various suitable crystals. Integrated circuits, including memories with millions of highly-ordered crystalline mineral lattice systems, can reasonably emulate the resonant functions of natural crystals with respect to receiving, storing, transforming, and radiating EM waves of specific frequencies.

While EM radiation emanating from the human body can be measured and recorded, large amounts of unnatural, ambient EM noise constantly surrounds most environments due to the presence of EM waves at multiple frequencies from high-powered radio communication and other modern technologies. The effect of ambient or directed EM upon any crystalline array depends on the resonant susceptibility of the specific array. The past century, beginning with the crystal radio leading up to the learned exploitation of the EM spectrum primarily for high-powered radio communication of ever increasing, higher frequencies, has created an omnipresent smog of unnatural ambient EM called noise. Therefore, Faraday cages are often used for any sensitive experiment that must filter out ambient EM noise, in order to have sufficient signal to noise ratio (SNR) for a successful reception, recording, storage and isolation of a radiated signal.

In contrast to conventional radio communication, which concentrates power at a particular frequency in the EM spectrum, subtle energy may instead be characterized by a broad but specific resonance and distribution of harmonics, sub-harmonics, and super-harmonics. Subtle energy resonance has also been linked to quantum energy fields and bioenergy fields, including vibrational resonance and vibrational interactions between crystalline structures of living tissue. The notion of a bioenergy field may include variations in electromagnetic fields generated by biological structures due to physiological activities and pathological states. A given subtle energy environment may include one or more sources of energy. Due to the resonance in the energy environment, the subtle energy may be responded to and/or regenerated by resonant objects. The energy environments may include various natural or synthetic, chemical, or biological crystalline elements, or any combinations thereof. Difficulties in studying subtle energy resonances may include ambient EM noise interference, lack of reliable instrumentation with respect to real-time detection, storage, and analysis. Thus, there is therefore also a long-standing need for an improved system, apparatus, and method for detecting, storing, and regenerating utilizing manifestations of subtle energy resonance. It is to be understood that the regeneration of subtle energy resonance signals includes re-emitting, rebroadcasting, reproducing, replaying, playback, re-radiating, or other suitable method of effecting manifestations of subtle energy resonance.

SUMMARY

This summary is provided to introduce a selection of concepts in a simplified form that are further described in the Detailed Description below. This summary is not intended to identify key features or essential features of the claimed subject matter, nor is it intended to be used as an aid in determining the scope of the claimed subject matter.

Some embodiments of the present disclosure include a system for recording subtle energy resonance, comprising: (a) an electromagnetic shield, (b) an antenna array disposed within the electromagnetic shield, the antenna array having at least one antenna, each antenna comprising: (i) a housing; (ii) a conductive disk, coupled to the housing, that receives at least one subtle energy resonance signal from a source; and (iii) an amplifier circuit board coupled to the conductive disk; (c) a multi-channel signal processor coupled to each antenna of the antenna array, the multi-channel signal processor converting the at least one subtle energy resonance signal into at least one digital subtle energy resonance signal; and (d) a memory coupled to at least one processor and the multi-channel signal processor, the processor storing the digital subtle energy resonance signals into the memory.

Various embodiments of the present disclosure include a method for capturing and recording subtle energy resonance signals, comprising: receiving a subtle energy resonance signal, via an antenna array, from a source, the antenna array having at least one antenna comprising: a housing, a conductive disk, and an amplifier; amplifying the subtle energy resonance signal, via the amplifier; converting, via a signal processor, the subtle energy resonance signal into a digital subtle energy resonance signal; transmitting, via the signal processor, the digital subtle energy resonance signal to a computing device having one or more processors and a memory; and storing, via the one or more processors, the digital subtle energy resonance signal into the memory.

In some embodiments, the present disclosure includes a system for regeneration of subtle energy resonance, comprising: (a) at least one processor; (b) a memory coupled to the at least one processor, the memory including at least one stored subtle energy resonance signal; (c) a signal processor communicatively coupled to the at least one processor and the memory, the signal processor having a digital-to-analog converter that converts the at least one stored subtle energy resonance signal into at least one analog subtle energy resonance signal; and (d) at least one antenna electrically coupled to the signal processor, each antenna of the at least one antenna including a spiral coil having a plurality of loops, such that each antenna regenerates the at least one analog subtle energy resonance signal.

BRIEF DESCRIPTION OF DRAWINGS

The accompanying drawings, where like reference numerals refer to identical or functionally similar elements throughout the separate views, together with the detailed description below, are incorporated in and form part of the specification, and serve to further illustrate embodiments of concepts that include the claimed disclosure, and explain various principles and advantages of those embodiments.

The methods and systems disclosed herein have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

DETAILED DESCRIPTION

Figure 1:
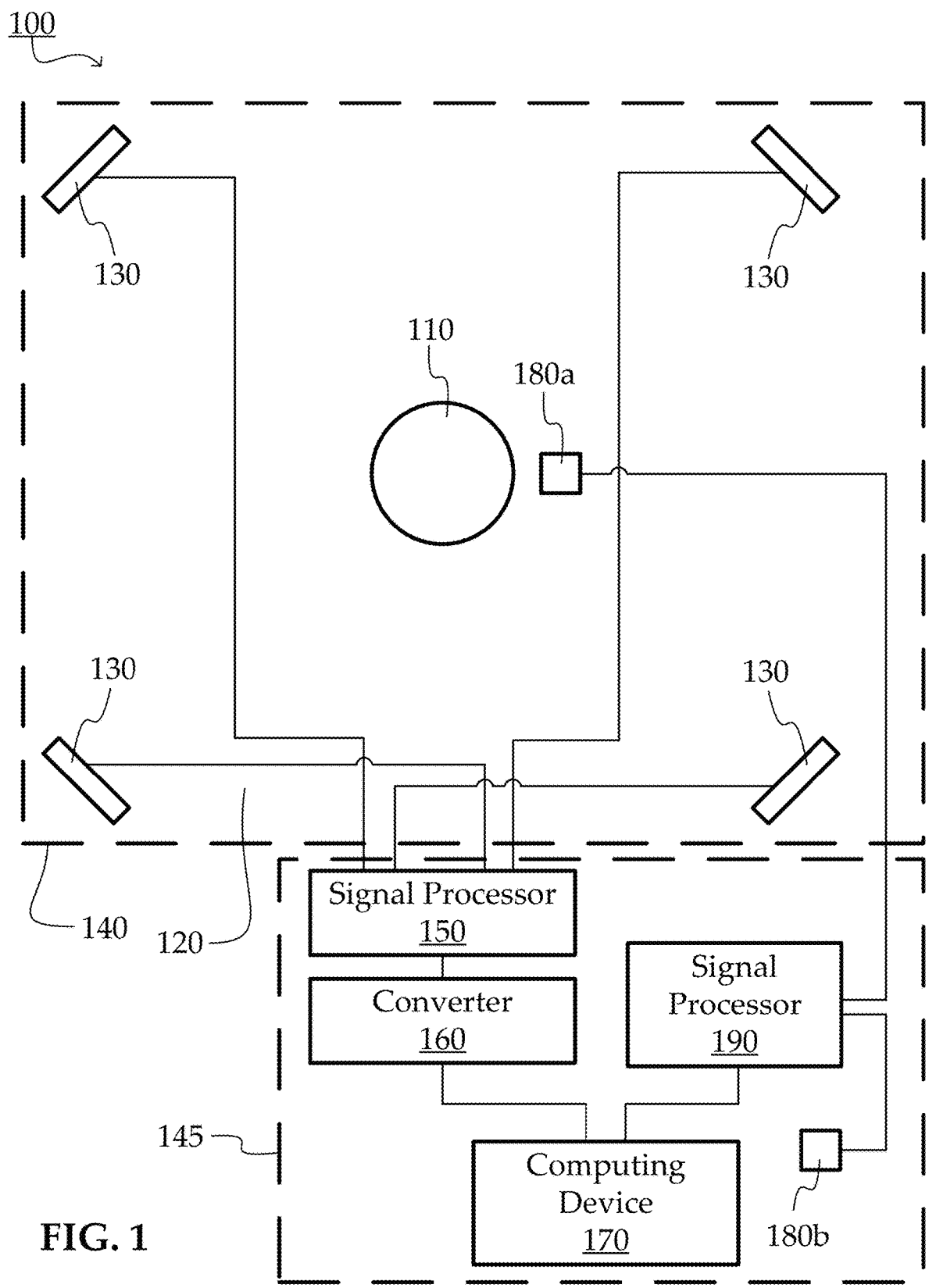
FIG. 1 is a system for capturing and recording subtle energy resonance signals, according to the present disclosure.

While this technology is susceptible of embodiment in many different forms, there is shown in the drawings and will herein be described in detail several specific embodiments with the understanding that the present disclosure is to be considered as an exemplification of the principles of the technology and is not intended to limit the technology to the embodiments illustrated. The terminology used herein is for the purpose of describing particular embodiments only and is not intended to be limiting of the technology. As used herein, the singular forms "a," "an," and "the" are intended to include the plural forms as well, unless the context clearly indicates otherwise. It will be further understood that the terms "comprises," "comprising," "includes," and/or "including," when used in this specification, specify the presence of stated features, integers, steps, operations, elements, and/or components, but do not preclude the presence or addition of one or more other features, integers, steps, operations, elements, components, and/or groups thereof. It will be understood that like or analogous elements and/or components, referred to herein, may be identified throughout the drawings with like reference characters. It will be further understood that several of the figures are merely schematic representations of the present technology. As such, some of the components may have been distorted from their actual scale for pictorial clarity.

The present disclosure generally relates to systems and methods of signal analysis and generative response. More specifically, the present invention focuses on control of manifestations of subtle energy resonance. An event that can be reliably detected and recorded, such as a change in value of natural electromagnetic radiation emanating from select human body subjects, may fall within this analysis and control. Reciprocally, intentional replication of an event detected and recorded should produce a determinable effect in subtle energy resonance.

The present disclosure is directed to various embodiments of systems and methods for recording, analyzing, manipulating, and producing subtle energy resonance signals. In some embodiments, the systems and methods include an antenna array to receive subtle energy resonance signals from a designated energy environment. The designated energy environment and the antenna array may be disposed within a multi-layer Faraday cage to protect against electromagnetic noise and to ensure the purity of the received subtle energy resonance signals. The antenna array is then coupled to a multi-channel signal processor and a computing device to process and to record the subtle energy resonance signals into a memory. In certain embodiments, the systems and methods include an antenna for short-range broadcasting of the recorded subtle energy resonance signals to affect the subtle energy resonance in a biological subject. Further aspects of the systems and methods will be described in greater detail below in reference to the figures.

FIG. 1 illustrates a block diagram of a subtle energy resonance recording system 100. In various embodiments, the system 100 includes at least one antenna 130 (collectively referred to as an antenna array), an electromagnetic (EM) Faraday cage shield 140, a second electromagnetic (EM) Faraday shield 145, a signal processor 150, a converter 160, and a computing device 170. In some embodiments, the system 100 further comprises a recording room microphone 180a and a reference microphone 180b communicatively coupled to a second signal processor 190. The system 100 provides accurate and real-time detection, recording, storage, and analysis of subtle energy resonance with minimal interference by ambient EM noise.

The at least one antenna 130 of the antenna array is directed at receiving subtle energy resonance signals emitted from a source 110 (e.g. a subtle energy resonance source) within a recording room. The source 110 may also be described as a biological agent, subject, or instrument of non-local quantum energy. In some embodiments, the source 110 is a human subject. It is to be understood that the source 110 is not limited to human subjects, but may also comprise other biological and non-biological matter that emits subtle energy resonance. The subtle energy resonance signals emitted from the source 110 alter an EM field disposed within an energy environment 120 contained within the EM Faraday cage shield 140. The changes in the EM field actuate the at least one antenna 130, such that the at least one antenna 130 receives the subtle energy resonance signals. The antenna array will be described in greater detail below and in reference to FIGS. 2-3.

The EM Faraday cage shield 140 includes an electrically conductive material that forms a Faraday cage with a separate signal processing room sharing a common shielded wall to protect the system 100 from EM interference. The cables are routed in a right angle crossing configuration to minimize undesired coupling of noise or crosstalk. The cables may comprise sets of twisted pairs within a multiple shielded sheath, which eliminates crosstalk and EMF interference. The EM Faraday cage shield 140 utilizes multiple isolated and insulated layers to reject common-mode coupling from inside to outside. The outermost layer is well grounded to the outside ground via a low impedance connection to a grounding rod, driven into Earth ground. The innermost layer is electrically isolated from ground. Having an innermost and outermost layer minimizes outside EMF interference, including AC noise, over a wide bandwidth of possible interfering signals. Isolation from infrasound band EMF interference is highest in a layered Faraday cage design, such as EM Faraday cage shield 140. As such, in one or more embodiments, the electrically conductive material is structured as a double-walled mesh or solid. As a result, the EM Faraday cage shield 140 can be used as an isolation chamber to test various commercial products that emit EMF interference or AC noise. In various embodiments, system 100 includes an EM Faraday cage shield 145 which includes an electrically conductive material to protect the system 100 from EM interference. The signal processor 150, converter 160, computing device 170, and signal processor 190 are disposed within the EM Faraday cage shield 145. It is to be understood that the EM Faraday cage shield 145 may be constructed the same or similar to the EM Faraday cage shield 140, as previously described, or may be composed of different material and be constructed with a different size and shape.

The signal processor 150 is communicatively coupled to the antenna array. The signal processor 150 comprises at least one input port that receives the captured subtle energy resonance signal from each of the at least one antenna 130. In certain embodiments, each of the at least one antenna 130 transmits the captured subtle energy resonance signal along an XLR cable. Each XLR cable may be coupled to a DB25 to XLR input cable, which is then coupled to the signal processor 150. In one or more embodiments, for example, the received signals are 24-bit signals at a fidelity of approximately 0 Hz to 65 Hz, with a high signal-to-noise ratio (SNR). The signal processor 150 may be coupled to the antenna array with a plurality of XLR cabling. The signal processor 150 may also provide the antenna array with power connected to a low noise FET amplifier signal processing board.

The signal processor 150 further includes an analog-to-digital (A/D) converter. The signal processor 150 converts the captured subtle energy resonance signal from analog into a digital subtle energy resonance signal suitable for processing and storage on the computing device 170. In some embodiments, the A/D converter samples the incoming analog signal at a sampling frequency of at least 192 kHz at 24-bit depth. One of ordinary skill in the art would understand an audio file sampled from a signal at 192 kHz at 24-bit depth to be a high resolution audio file. It is to be understood that the signal processor 150 may also be known as an audio interface.

In certain embodiments, the system 100 comprises the converter 160 which includes one or more inputs having a first type of port, and one or more outputs having a second type of port. For example, the converter 160 may receive a signal using a Peripheral Component Interconnect (PCI) input port, and may transmit the signal using a Thunderbolt output port. It is to be understood that other suitable protocols may be used for the input and output, such as PCI Express, Universal Serial Bus (USB), USB-C, Firewire, or other suitable protocol to communicate between the signal processor 150 and the computing device 170.

The computing device 170 is communicatively coupled to, and receives the subtle energy resonance signal from, the signal processor 150. In certain embodiments, the computing device 170 is coupled to the signal processor 150 via the converter 160. An example computing device 170 is shown and described in FIG. 13, including at least one processor and a memory. The computing device 170, via the at least one processor, receives the digital subtle energy resonance signal from the signal processor 150 or the converter 160. The computing device 170 then stores the digital subtle energy resonance signal into memory for later regeneration. The computing device 170 may also tune, filter, adjust one or more features of, or otherwise enhance the subtle energy resonance signal prior to or after storage in memory.

In one or more embodiments, the system 100 further comprises the recording room microphone 180a, the reference microphone 180b, and the second signal processor 190. Each voice recording microphone 180a, 180b may comprise cardioid condenser microphones, or other suitable microphones for receiving acoustic signals as reference only, for the benefit of a time signature. The recording room microphone 180a is mounted to a ceiling towards a center of the recording room to capture a recording room acoustic signal emitted from the source 110. It is to be understood that the recording room microphone 180a may be disposed at any suitable location within the EM Faraday cage shield 140 to record acoustic signals from the source 110. The reference microphone 180b is disposed within the signal processing room, the reference microphone 180b capturing a reference acoustic signal.

The second signal processor 190 may be coupled to the recording room microphone 180a, the reference microphone 180b and the computing device 170. The second signal processor 190 receives the recording room acoustic signal and the reference acoustic signal from the recording room microphone 180a and the reference microphone 180b, respectively. The second signal processor 190 may have similar functions to the signal processor 150, such as converting the analog acoustic signals into digital acoustic signals, and transmitting the digital acoustic signals to the computing device 170. The computing device 170 processes and stores the digital recording room acoustic signal and the digital reference acoustic signal into memory. The second signal processor 190 may also couple to the recording room microphone 180a and the reference microphone 180b.

In some embodiments, the computing device 170 records subtle energy resonance signals separately from each antenna 130. In an example with a first, a second, a third, and a fourth antenna, the computing device 170 receives a first, a second, a third, and a fourth digital subtle energy resonance signal.

Figure 2:
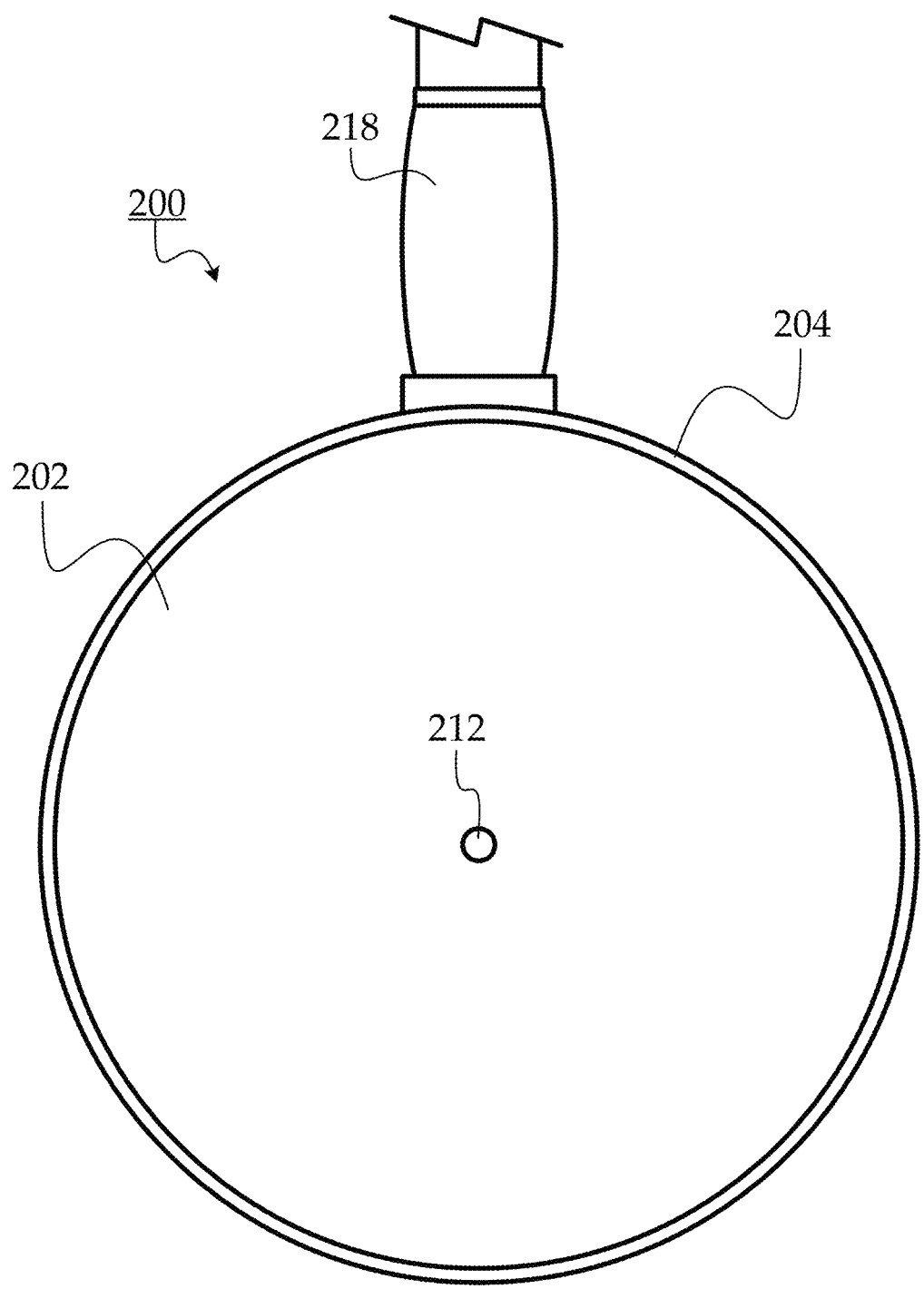
FIG. 2 illustrates a front view of an exemplary antenna for capturing subtle energy resonance signals, according to the present disclosure.
Figure 3:
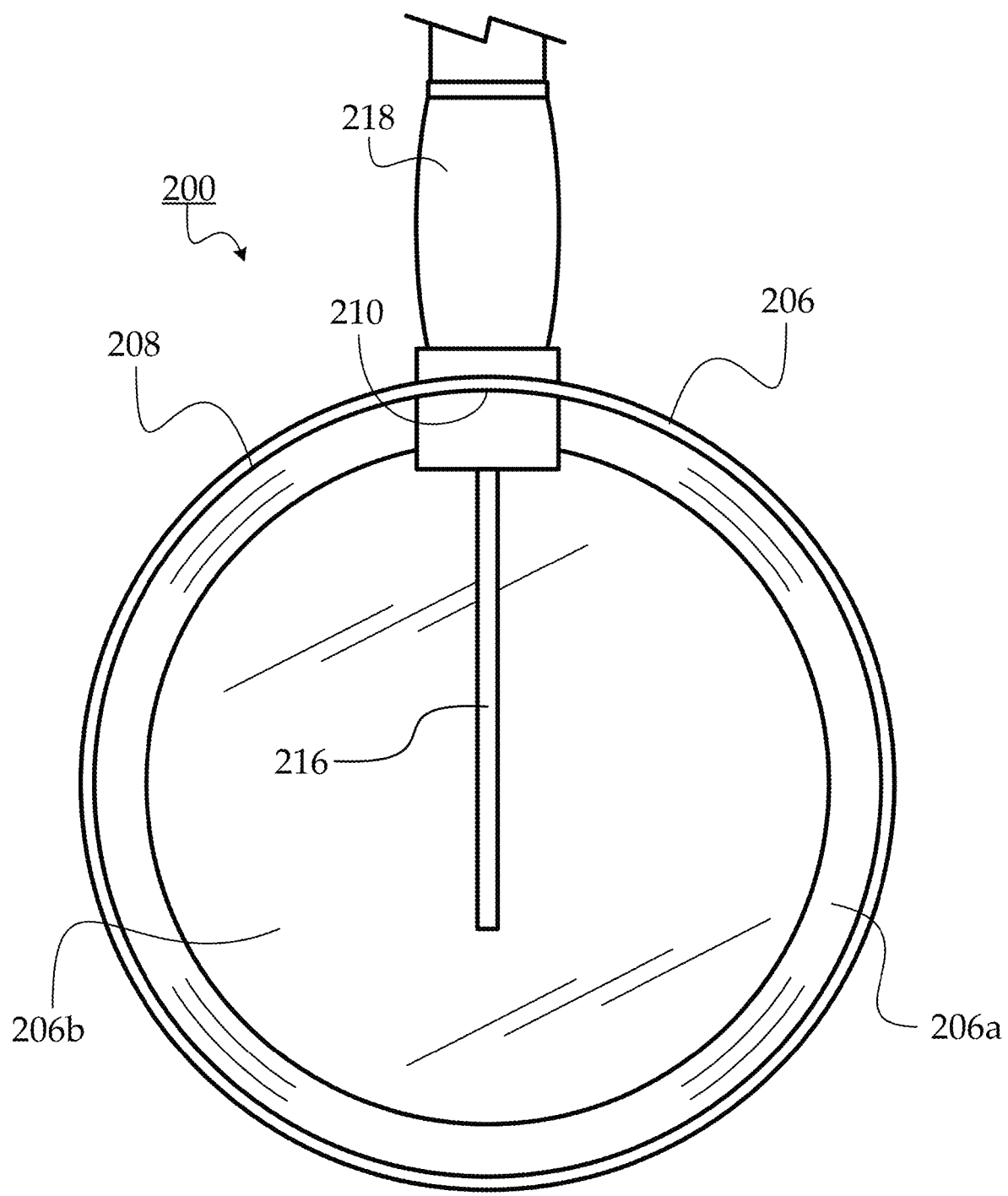
FIG. 3 depicts a front view of the exemplary antenna of FIG. 2 with a sensor plate cover removed, according to the present disclosure.

FIGS. 2-3 depict exemplary views of an antenna 200 that may be used as the antenna 130. In various embodiments, the antenna 200 includes a sensor plate cover 202, a housing 204, a contact lead 212, a mounting plate 214, a signal processing circuit board 216, and an XLR cable 218. In some examples, the housing 204 includes a body 206, an upper opening 208 and an aperture 210. The body 206 may have a side wall 206a and a bottom portion 206b, and be made of a thin, solid aluminum, or any other suitable conductive material to create a partial Faraday cage surrounding the signal processing circuit board 216. It is to be understood that the body 206 of the housing 204 may be constructed to have any size or shape, or be made of any suitable material, to facilitate receiving subtle energy resonance signals with minimal interference. The antenna 200 detects changes in local EM fields as subtle energy resonance signals.

As shown in FIG. 2, the sensor plate cover 202 acts as a sensing antenna, which may be constructed as an electrically conductive disk coupled to housing 204. The sensor plate cover 202 is coupled to the upper opening 208, and the contact lead 212. Changes in the local EM field, or fluctuations in SU(2)/U(1) mixed gauge symmetries, will manipulate charges in the sensor plate cover 202, which will transmit a detected analog signal to the contact lead 212.

As shown in FIG. 3, the contact lead 212 is coupled to the signal processing circuit board 216. The signal processing circuit board 216 receives subtle energy resonance signals from the sensor plate cover via the contact lead 212. The signal processing circuit board 216 acts as a low noise, signal conditioning Field-Effect Transistor (FET) receiver circuit board that amplifies the received subtle energy resonance signal for transmission along the XLR cable 218. The signal processing circuit board 216 may have one or more FETs having high input impedance and low output impedance, which are regulated by an applied power. The antenna 200 is thus capable of adjusting amplitude of the received subtle energy resonance signal before transmitting the signal via the XLR cable 218.

In one or more embodiments, the sensor plate cover 202 acts as a sensing scalar wave antenna. Scalar waves may be understood as longitudinal waves of potentials having a combination of a vector potential and a scalar potential. The sensor plate cover 202 acts as a flat surface condenser which may interact with one or more scalar waves. In various embodiments, the subtle energy resonance signals may comprise one or more scalar wave resonant functions.

Figure 4:
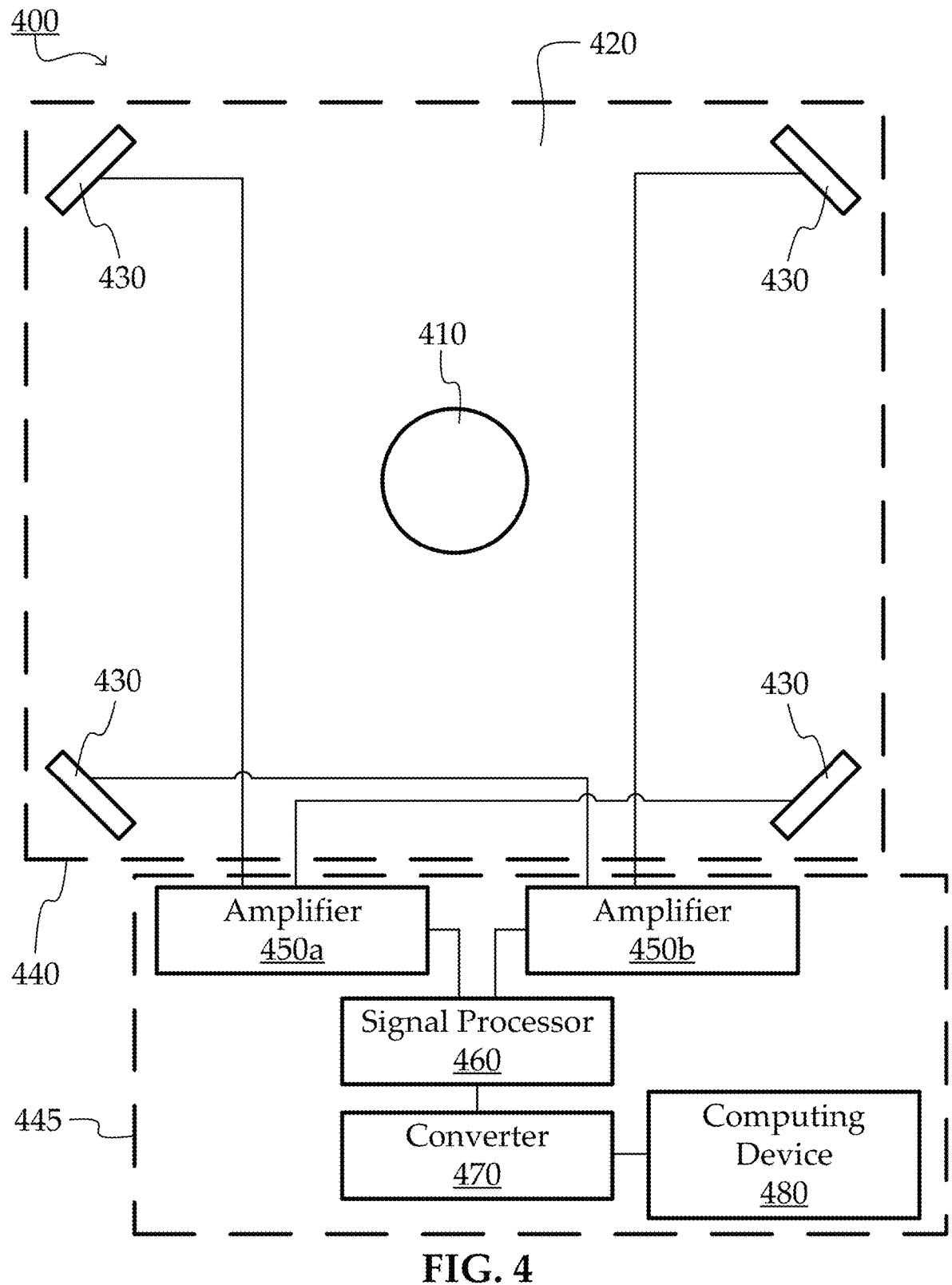
FIG. 4 is a system for regeneration of stored subtle energy resonance signals, according to the present disclosure.

FIG. 4 illustrates a block diagram of a subtle energy resonance regeneration system 400. In various embodiments, the system 400 includes at least one antenna 430 (scalar or EM antenna), an EM Faraday cage shield 440, an EM Faraday cage shield 445, a first amplifier 450a, a second amplifier 450b, a signal processor 460, a converter 470, and a computing device 480. The system 400 affects subtle energy resonance of a subject 410 with a stored subtle energy resonance signal amplified and regenerated through the at least one antenna 430. It is to be understood that the EM shield 440, the EM Faraday cage shield 445, the signal processor 460, the converter 470, and the computing device 480 may be the same, or have similar components and functionality, as the EM shield 140, the EM Faraday cage shield 145, the signal processor 150, the converter 160, and the computing device 170, respectively. It is also to be understood that the regeneration of subtle energy resonance signals includes re-emitting, rebroadcasting, reproducing, replaying, playback, re-radiating, or other suitable method of effecting manifestations of subtle energy resonance. Furthermore, the regenerated subtle energy resonance emitted from the at least one antenna 430 is dependent on the regeneration of the same high fidelity of the original subtle energy resonance recorded by the system 100.

The computing device 480 comprises subtle energy resonance signals stored in memory. In some embodiments, the computing device 480 is communicatively coupled to the converter 470 and transmits the stored subtle energy resonance signals to the signal processor 460 via the converter 470 for regeneration. In other embodiments, the computing device 480 may be directly coupled to the signal processor 460. The stored subtle energy resonance signals are stored in digital format, and may be stored as a 24-bit Pulse Code Modulation (PCM) audio file or other suitable audio format for storing high quality signals. An example computing device 480 is shown and described in FIG. 13.

The converter 470 includes one or more inputs having a first type of port, and one or more outputs having a second type of port. For example, the converter 470 may receive a signal using a Thunderbolt input port, and may transmit the signal using a PCI output port. It is to be understood that other suitable protocols may be used for the input and output, such as PCI Express, USB, USB-C, Firewire, or other suitable protocol to communicate between the signal processor 460 and the computing device 480.

The signal processor 460 receives the stored energy resonance signal from the computing device 480. The signal processor 460 may include a digital-to-analog (D/A) converter that converts the received stored subtle energy resonance signal from a digital to an analog subtle energy resonance signal suitable for regeneration through the at least one antenna 430.

The signal processor 460 is communicatively coupled to the first amplifier 450a and the second amplifier 450b. The first amplifier 450a and the second amplifier 450b receive subtle energy resonance signals from the signal processor 460 for regeneration. In an example embodiment in which the at least one antenna 430 comprises four antennae, four outputs (one for each of the at least one antenna 430) of the signal processor 460 are each coupled to separate channels. The separate channels may comprise mono D-subminiature (D-sub) to RCA cables. In some embodiments, a first and a second channel of the separate channels are coupled to a left and right input on the first amplifier 450a, respectively. A third and fourth channel of the separate channels may be coupled to a left and right input on the second amplifier 450b, respectively. It is to be understood that a number of amplifiers coupling the signal processor 460 to the at least one antenna 430 may vary depending upon the number of antenna.

The first amplifier 450a and the second amplifier 450b amplify the received subtle energy resonance signal prior to transmitting the signal to the at least one antenna 430. In some embodiments, the first amplifier 450a and the second amplifier 450b are dual channel FET amplifiers with four channel amplification. In the example embodiment with four antennae, the first amplifier 450a is communicatively coupled to a first and a second antenna, and the second amplifier 450b is communicatively coupled to a third and a fourth antenna. The first amplifier 450a and the second amplifier 450b may be coupled to the at least one antenna 430 via XLR cables spliced at an amplifier connection point.

In various embodiments, the at least one antenna 430 are disposed in each corner of the EM Faraday cage shield 440, which may be the same EM Faraday cage shield as the EM Faraday cage shield 140 used for recording. An exemplary antenna that may be used as one of the at least one antenna 430 is shown and described in FIG. 5. The at least one antenna 430 receives an amplified subtle energy resonance signal from either the first amplifier 450a or the second amplifier 450b, and radiates the amplified subtle energy resonance signal towards a subject 410 in an energy environment 420, thus affecting the subtle energy resonance of the subject 410.

Figure 5:
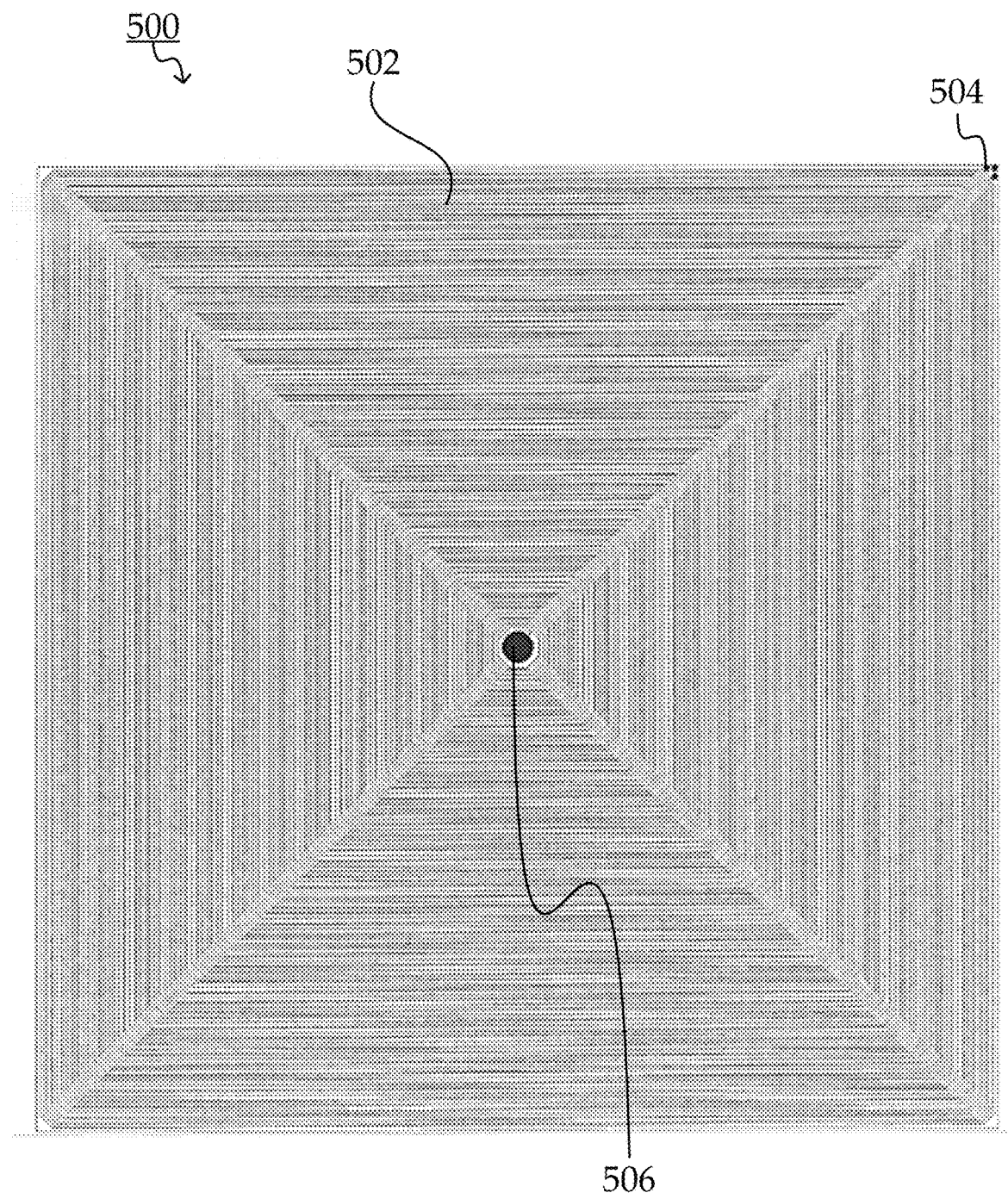
FIG. 5 is a representation of an exemplary signal regeneration pancake coil antenna, according to the present disclosure.

FIG. 5 illustrates a representation of a multi-turn, pancake spiral coil 500 that may be used in the at least one antenna 430 or 130. In one or more embodiments, the coil 500 comprises a plurality of loops 502 and electrical contact leads 504, 506. The coil 500 may comprise any suitable electrically conductive wire or etched conductive PCB trace leads for conducting a subtle energy resonance signal and generating a subtle energy resonance field from the subtle energy resonance signal. Furthermore, the plurality of loops 502 may comprise any number of loops, at any suitable density, size or shape for radiating the stored, transmitted, and amplified subtle energy resonance signal and affecting subtle energy resonance of the subject 410. In one or more embodiments, each loop of the plurality of loops 502 comprises a predetermined ratio between a predetermined height and predetermined width of each loop.

In various embodiments, the antenna 200 may be used as the at least one antenna 430 or 130. The antenna 200 as shown in FIGS. 2-3 may be configured to act as either a scalar antenna receiver, such as antenna 130, or a scalar antenna transmitter, such as antenna 430, that receives or transmits longitudinal electromagnetic waves.

Figure 6:
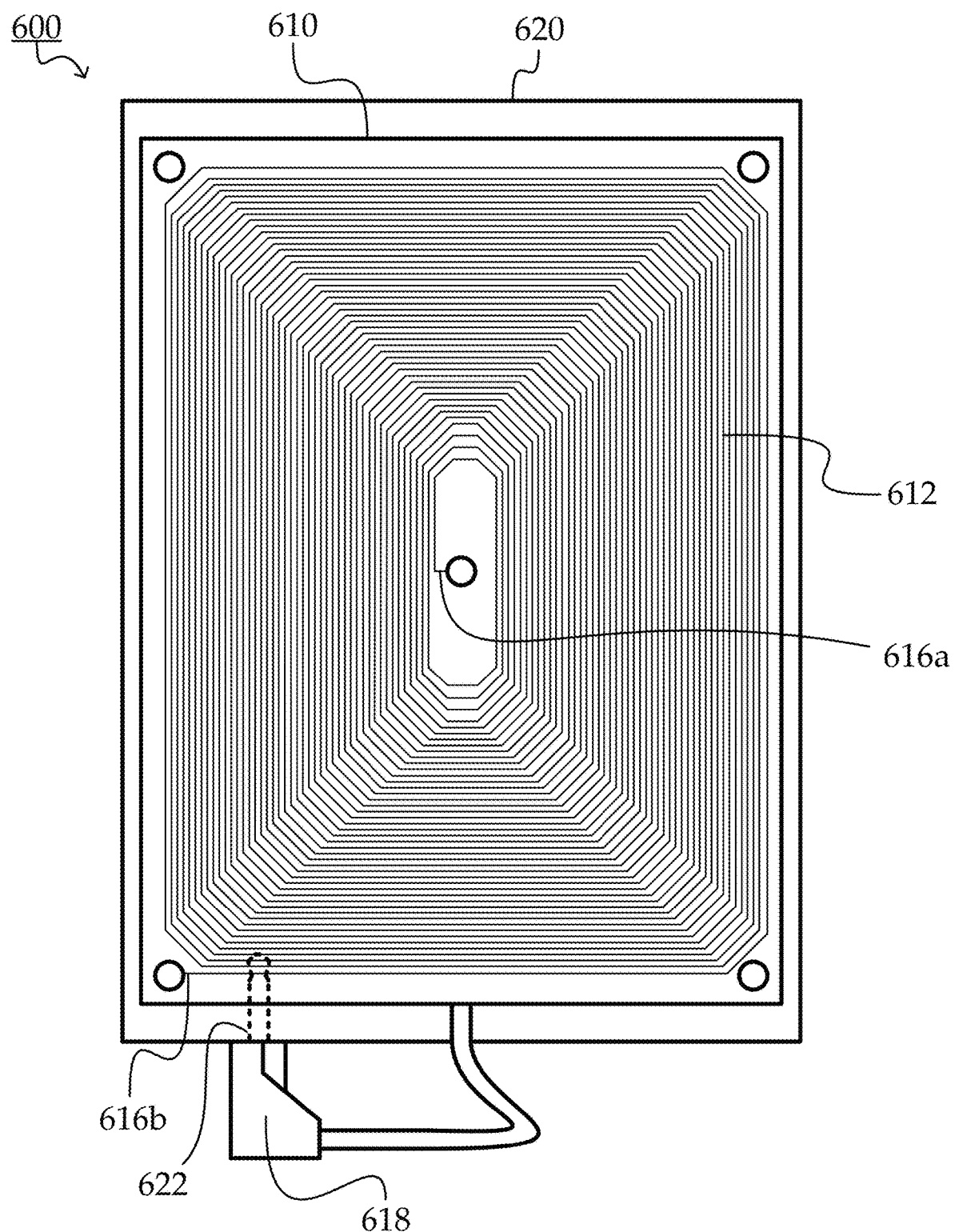
FIG. 6 shows a front view of an exemplary portable regeneration antenna and digital regeneration device.

FIG. 6 depicts an exemplary portable subtle energy resonance regeneration system 600 having an antenna 610 coupled to a digital regeneration device 620. The portable subtle energy resonance regeneration system 600 emits a subtle energy resonance signal to a localized area. Thus, in various embodiments, the portable subtle energy resonance regeneration system 600 affects the subtle energy resonance of a subject without requiring a connection to external power or another device. The subtle energy resonance emitted from the portable subtle energy resonance regeneration system 600 is dependent on the regeneration of the same high fidelity of the original subtle energy resonance recorded by the system 100. Furthermore, the radiated electromagnetic field (EMF) from a portable subtle energy resonance regeneration system of the present disclosure has been tested. The results confirm a 20 dB lower amplitude than the EMF radiation from a common cell phone or laptop computer, which was also measured. In addition, the reduction in the AC noise levels were also verified using an AC Gaussmeter made by Integrity Design and Research, Inc.

In one or more embodiments, the digital regeneration device 620 is a handheld high-resolution audio player having at least one processor, a memory, a power source, and featuring a Burr Brown or equivalent digital-to-analog converter capable of regeneration of 24-bit, 192 kHz PCM audio files. A stored subtle energy resonance signal is transferred from a data storage, such as data storage 750 described below, into the memory of the digital regeneration device 620. For example, the digital regeneration device 620 may be coupled via USB cable to a computing system used for signal capture, such as computing device 170. Capture software stored in a memory of the computing device is executed by a processor to export a predetermined subtle energy resonance signal as a full resolution, 24-bit, 192 kHz PCM Waveform Audio File Format (WAV) file. It is to be understood that the stored subtle energy resonance signal may be formatted in any file format suitable for the digital regeneration device 620. The digital regeneration device 620 receives the subtle energy resonance signal and stores the signal into the memory of the digital regeneration device 620 for regeneration. Furthermore, the power source may be a rechargeable lithium polymer battery, or other suitable battery for portable use.

The antenna 610 includes a multi-turn, pancake spiral coil 612 that conducts a subtle energy resonance signal. In some embodiments, the coil 612 is disposed on a printed circuit board (PCB) 614 and made of any suitable conductive material. The coil 612 may be rectangular in shape, or any other suitable size and shape for affecting the subtle energy resonance of the subject. Furthermore, the coil 612 may have any suitable number of rotations. Leads 616a, 616b are coupled to and powered by the digital regeneration device 620 via a 3.5 mm headphone jack 618 and a 3.5 mm headphone jack socket 622. In particular, lead 616a at the center of the coil 612 is coupled to a first lead of the 3.5 mm headphone jack 618. The lead 616b at a corner of the coil 612 is coupled to a second lead of the 3.5 mm headphone jack 618. It is to be understood that any suitable configuration of audio connector may be used in place of the 3.5 mm headphone jack 618 and the 3.5 mm headphone jack socket 622. In one or more embodiments, the antenna 610 is coupled to and mounted on a first portion of the digital regeneration device 620.

The digital regeneration device 620 transmits the subtle energy resonance signal stored in memory to the antenna 610 via the 3.5 mm headphone jack 618. The regeneration antenna 610 emits the subtle energy resonance signal outwards, away from a face of the coil 612, to affect the subtle energy resonance of the subject proximate to the portable subtle energy resonance regeneration system 600. In one or more embodiments, the subject is a predetermined distance away from the regeneration antenna 610 during regeneration and in a particular orientation with respect to the regeneration antenna 610 (for example, perpendicular to a face of the regeneration antenna 610 or in front of a face of the regeneration antenna 610), where the predetermined distance may be dependent upon the size of the coil, amplification in the system 600, and/or other suitable factors. The regenerated subtle energy resonance signal comprises EM energy within the audio spectrum at a bandwidth and clarity of signal without amplification of EMF interference or introduction of A/C noise to maintain the fidelity of the original signal.

Figure 7:
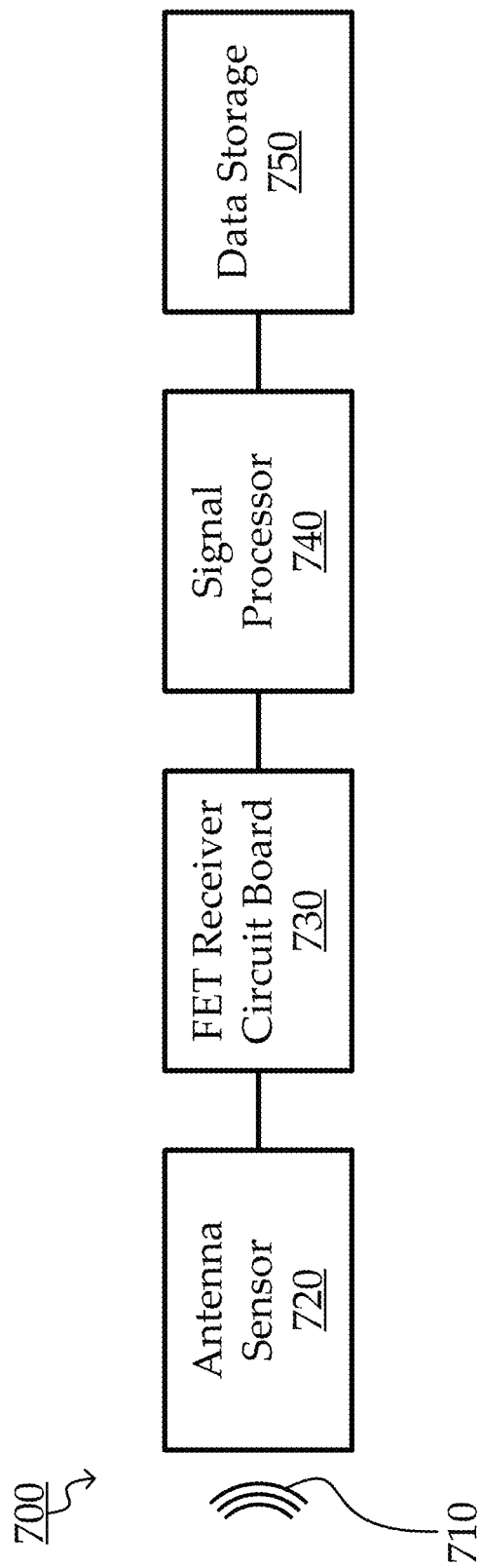
FIG. 7 is a simplified block diagram of the system for capturing and recording subtle energy resonance signals, according to the present disclosure.

FIG. 7 is a simplified block diagram of the system 700 for capturing and recording subtle energy resonance signals of FIG. 1. The system 700 includes subtle energy resonance signals 710 received by an antenna sensor 720. In one or more embodiments, the antenna sensor 720 comprises the sensor plate cover 202. The antenna sensor 720 transmits the captured subtle energy resonance signal to a FET receiver circuit board 730, or other suitable on-board signal processor for amplifying the captured subtle energy resonance signal. The FET receiver circuit board 730 may comprise the signal processing circuit board 216.

A signal processor 740 receives the captured and amplified subtle energy resonance signal from the FET receiver circuit board 730, and converts the received signal into a digital subtle energy resonance signal. In certain embodiments, the signal processor 740 is the signal processor 150. The signal processor 740 then transmits the digital subtle energy resonance signal to data storage 750 for later regeneration. The data storage 750 may be a memory disposed within the computing device 170.

Figure 8:
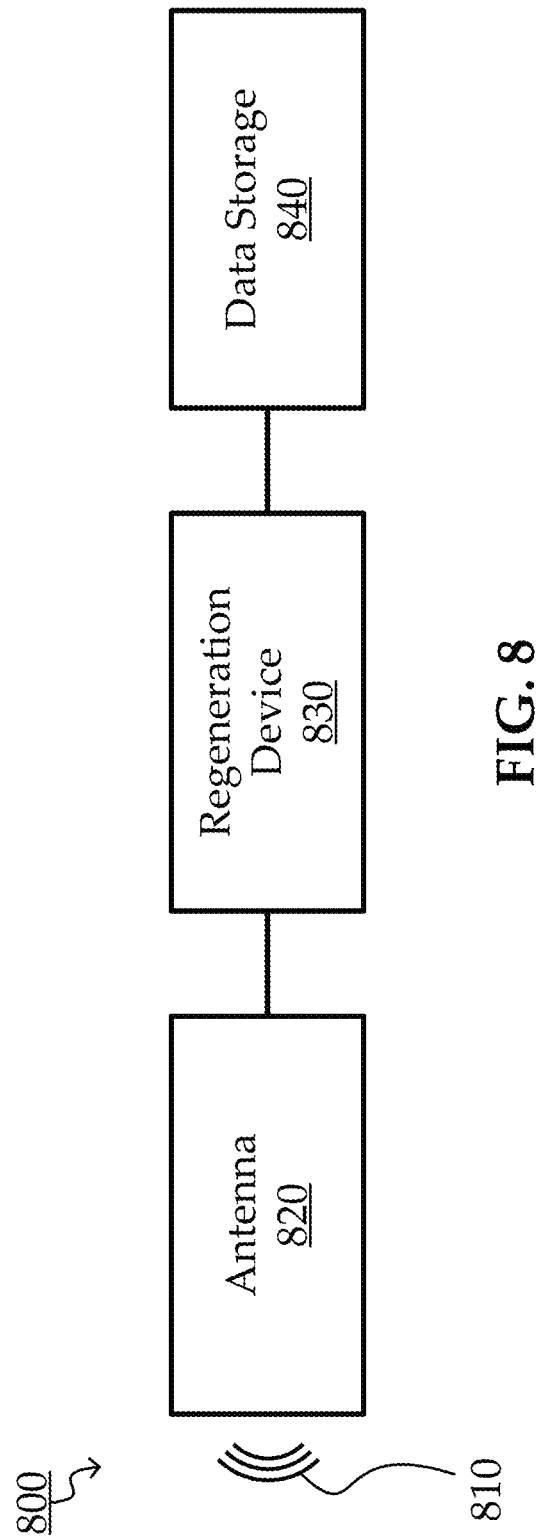
FIG. 8 is a simplified block diagram of the system for regeneration of stored subtle energy resonance signals, according to the present disclosure.

FIG. 8 is a simplified block diagram of the system 800 for regeneration of subtle energy resonance signals. In certain embodiments, the system 800 represents either the regeneration system of FIG. 4 or the portable regeneration system of FIG. 5. Digital subtle energy resonance signals are stored in a data storage 840 as a full resolution 24-bit, 192 kHz PCM WAV file, or other suitable format. The data storage 840 may comprise either the memory disposed within the computing device 480 or the memory coupled to the digital regeneration device 620. In some embodiments, the data storage 840 may be the same data storage as the data storage 750, or may comprise digital subtle energy resonance signals transferred from the data storage 750.

A regeneration device 830 receives the stored subtle energy resonance signal from the data storage 840, converts the stored subtle energy resonance signal into an analog subtle energy resonance signal, and transmits the analog subtle energy resonance signal to the antenna 820. In one or more embodiments, the regeneration device 830 comprises the signal processor 460, the first amplifier 450a and the second amplifier 450b. In other embodiments, the regeneration device 830 comprises the digital regeneration device 620. The antenna 820 then radiates the subtle energy resonance signal 810 to affect the subtle energy resonance of a subject. The antenna 820, which may be referred to herein as a regeneration antenna, may comprise either the at least one antenna 430 or the antenna 610.

Figure 9:
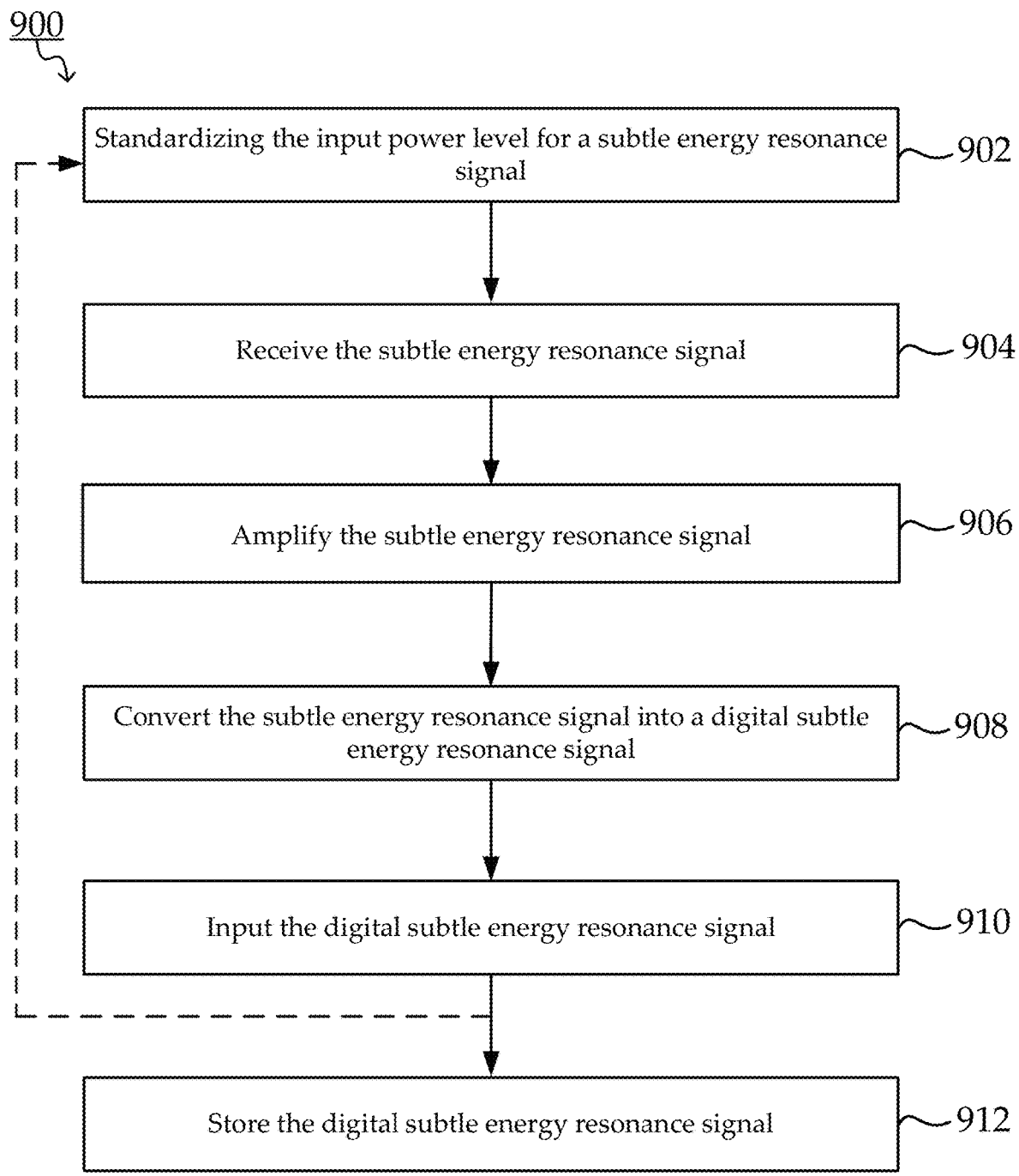
FIG. 9 is a flowchart showing a method for recording subtle energy resonance signals, according to the present disclosure.

FIG. 9 is a flow diagram showing a method 900 for capturing and recording subtle energy resonance signals, according to an example embodiment. The method 900 can be implemented using the capturing and recording system 100 shown in FIG. 1. In block 902, the method 900 can commence with standardizing the input power level for a subtle energy resonance signal.

In block 904, the method 900 includes receiving the at least one subtle energy resonance signal via at least one antenna, such as the at least one antenna 130. In block 906, the method 900 optionally includes amplifying, via at least one amplifier, the at least one subtle energy resonance signal prior to transmission to a signal processor. The amplifier may comprise an amplifier circuit such as the signal processing circuit board 216. In block 908, the method 900 includes converting the at least one subtle energy resonance signal from an analog signal to at least one digital subtle energy resonance signal via a signal processor, such as signal processor 150. In block 910, the method 900 includes inputting the at least one digital subtle energy resonance signal to a computing device, such as an exemplary computing device shown in FIG. 13 or the computing device 170. Block 910 may further include analyzing the amplitude and frequencies of the at least one digital subtle energy resonance signal to initially standardize an input power level for all recorded subtle energy resonance signals by applying appropriate filtering. Amplification of the subtle energy resonance signals at block 906 may appropriately be adjusted to control the quality of the incoming signal. The dashed arrow in FIG. 9 represents optionally standardizing the input power level for the recorded subtle energy resonance signals and commencing again at block 902. In block 912, the method 900 includes storing the at least one digital subtle energy resonance signal into memory. Storing the at least one digital subtle energy resonance signal may include mixing each of the at least one digital subtle energy resonance signal into a single mono, stereo, or quad file for regeneration. In certain embodiments, the single stereo file is a single stereo 192 kHz at 24-bit depth file.

Figure 10:
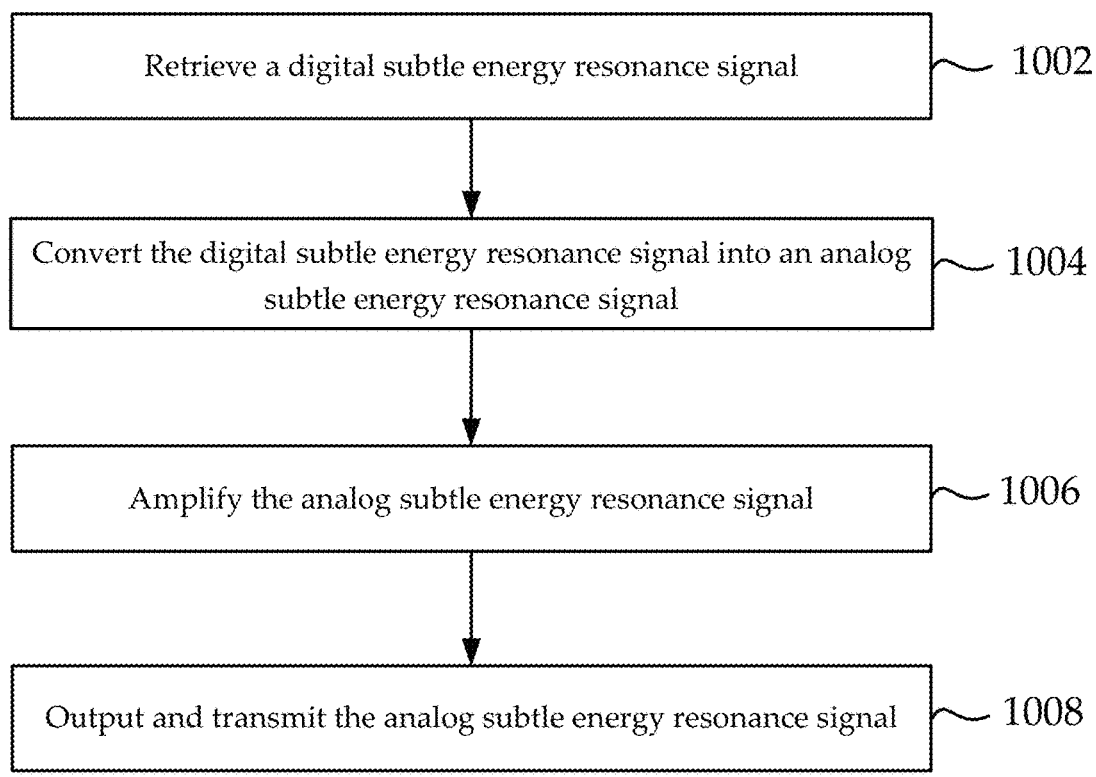
FIG. 10 is a flowchart showing a method for regeneration of subtle energy resonance signals, according to the present disclosure.

FIG. 10 is a flow diagram showing a method 1000 for regeneration of subtle energy resonance signals, according to an example embodiment. The method 1000 can be implemented using the system 400 shown in FIG. 4, or the system 600 shown in FIG. 6. In block 1002, the method 1000 can commence with retrieving, via at least one processor, a stored subtle energy resonance signal from a memory or data storage. The at least one processor and the memory or data storage may correspond to the computing device 480, for example. In block 1004, the method 1000 includes converting, via a signal processor, the stored subtle energy resonance signal from a digital signal to an analog subtle energy resonance signal. In some embodiments, the signal processor is the signal processor 460, or in other embodiments the signal processor is the digital regeneration device 620. In block 1006, the method 1000 optionally includes amplifying, via an amplifier, the analog subtle energy resonance signal. In certain embodiments, the amplifier includes the first amplifier 450a or the second amplifier 450b. In block 1008, the method 1000 includes outputting and transmitting, via an antenna, the analog subtle energy resonance signal to affect the subtle energy resonance of a subject. The antenna, in some embodiments, comprises the at least one antenna 430, or the antenna 610.

In various embodiments, the subtle energy resonance regeneration system of 4.6, 10 is used to charge water with one or more subtle energy resonance signals. One or more of the methods of the present disclosure may be used to regenerate the one or more subtle energy resonance signals applied to the water. Studies described below illustrate that charged water, water that has been subject to the one or more subtle energy resonance signals, enhances the growth of bacterial cultures after an initial inhibition of growth, due to acclimation. Studies also show that charged water increases the conductivity of human DNA. The charged water may be used in growing crops, farming, agriculture, raising of livestock, and general consumption by people for personal wellness.

Clinical Study Measuring Effects of Subtle Energy Resonance System on Bacterial Cultures As described in Appendix A entitled, "The Effects of Chi Box Technology on Bacterial Cultures in the Laboratory" by Beverly Rubik, Ph.D., and Harry Jabs, M.S., the effectiveness of the subtle energy resonance regeneration system according to the present disclosure was clinically investigated for its ability to facilitate growth of wild type *E. coli* bacteria cultures in the laboratory. This clinical study was conducted to investigate whether subtle energy resonance regeneration frequencies have an effect on heat-shocked (stressed) bacteria cultures to look for an impact on the culture growth of the well-known microbe, *E. coli*. In addition, a further clinical study was conducted on healthy growing bacterial cultures (not heat-shocked) for comparison.

A bioassay that had previously shown positive effects on culture growth from Reiki healer treatments which involved heat-shocked cell cultures was used. Both heat-shocked cultures and healthy cultures were studied in short and long-term clinical studies with the subtle energy resonance regeneration system. Long-term clinical studies utilized simultaneous measurements of light scattering from the bacterial cultures using real-time computer data acquisition.

In particular, five clinical studies were done using two different research designs: (1) Bacterial colony counts via plate count assay were done in three clinical studies; and (2) Light scattering from the turbid liquid bacterial cultures was assessed in two clinical studies. Whereas the plate count assay shows short-term effects on culture growth, the light scattering assay is capable of showing long-term effects of the treatment on culture growth.

Preparation of the Bacterial Cultures

The standard wild type strain (K12) of *E. coli* bacteria purchased from a culture collection corporation (Microbiologics, St. Cloud, Minn.) was inoculated into aqueous nutrient broth and incubated on a rotating water bath overnight at 37 C (human body temperature, the optimal temperature for *E. coli*). This initial culture was inoculated into 50 ml liquid minimal medium to support growth of *E. coli* (Vogel-Bonner-citrate solution with 1% D-glucose as carbon source). This stock culture was grown overnight in the rotating water bath at 37 C and was the inoculum used in all clinical studies. Fresh cultures of *E. coli* were grown overnight on minimal medium to mid-logarithmic growth phase for each clinical study. Each culture was centrifuged, washed, and resuspended in fresh liquid medium, and the absorbance at 600 nm, an indicator of culture density, was measured in a UV-visible spectrophotometer. Absorbance was adjusted to 0.15-0.3 by dilution with fresh minimum medium. Five ml of bacterial suspension of this stock culture was transferred into 6 sterile clear polycarbonate culture test tubes with plastic caps. Three culture samples were randomly assigned to the test group (subtle energy resonance regeneration treatment) and to the control group and labeled accordingly, such that triplicate samples were used for each condition. These constituted the culture samples to be used in the daily clinical studies.

For heat-shock clinical studies, the culture samples were placed in a water bath at 50 C for 25 min. This temperature and exposure time had been previously determined to inactivate (i.e., kill) 50% of the *E. coli* bacteria, which is known as the LD50 (lethal dose for 50% of the bacteria).

Three different types of clinical studies were done: (1) plate count assay following heat shock; (2) light-scattering assay on heat-shocked bacterial cultures over time; and (3) lightscattering assay on normal bacterial cultures (not heat shocked) over time.

Plate Count Assay to Count Viable Bacteria

In previous studies, Reiki masters and other healers had been shown to stimulate bacterial growth following heat shock using the following bioassay. The same research protocol was repeated here, except that no healers were used; instead, the subtle energy resonance regeneration treatment was used. Immediately after the heat shock, bacterial culture tubes were removed from the hot water bath. Cultures to be treated by the subtle energy resonance regeneration were placed in a rack, uncovered, and a bottom portion of the regeneration system was centered over the open test tubes, such that the bottom of the regeneration system was 2.5 inches from the bacteria. The regeneration system was set to 120, the highest intensity. The control culture samples were placed in a test tube rack in another room 10 to 15 feet from the treatment group and remained there for the duration of the treatment. The treatment times used varied from 12 minutes to 36 minutes, according to the four treatment programs of the regeneration system. One of the four subtle energy resonance regeneration treatments was selected for each clinical study.

After the treatment period, the culture samples were placed in a 37 C shaking water bath for 75 minutes of recovery and growth. Then the culture samples were placed in an ice water bath at 0 C for three minutes to stop growth. Following that, the culture samples were diluted 1:10 with phosphate-buffered saline (0.05M sodium-potassium phosphate with 0.15M NaCl), a standard solution used to dilute bacterial cultures for the plate count assay. Serial dilutions of 1:10 were made 5 times, such that a final dilution of the bacterial cultures of 1 part in 10E-5 was obtained.

A 0.1 ml aliquot of the final dilution of each culture sample was plated using sterile technique onto duplicate plates containing 3% agarose/nutrient broth. This is the standard plate count assay to determine the number of living bacteria present, measured by counting the number of colonies that grow on the plates. The plates were placed into an incubator overnight maintained at 37 C. The bacterial colonies that resulted from the growth of single cells on each plate were then counted 3 to 5 times each using an automated colony counter. The plate count values for test and control conditions were each averaged, standard deviations calculated, and the data analyzed for statistical significance.

Light Scattering Assay Procedures

Sample cultures were prepared as described previously. Treated and control cultures were placed on a 37 C shaking water bath for the duration of the clinical study. At various time intervals up to 3+ hours, the sample cultures were placed within a device consisting of an aluminum block with sample wells inside a dark chamber with LEDs (light-emitting diodes) and detectors for simultaneous light-scattering measurements. The light scattered from the cultures at a 90 degree angle to the incident light beams passed through a red (600 nm) filter and light-sensitive PIN diodes (p-type, intrinsic, and n-type layered semiconductors) were used as sensitive light detectors.

Real-time data acquisition was used to collect the data as optical signals from each culture, which were amplified, processed, and recorded simultaneously on a computer. Immediately after each timed measurement, cultures were returned to the 37 C water bath for further growth. By this means, the culture samples were measured simultaneously approximately every 30 minutes to yield seven measurements over 3 or more hours to look for any changes following subtle energy resonance regeneration treatment compared to controls. This method should amplify any differences between the treatment and control cultures over time. In one clinical study conducted using this method, heat-shocked bacterial cultures were studied; in another clinical study on another day using this method, normal bacterial cultures were studied.

Clinical Studies Performed

Five clinical studies were performed over five days: (1) S101, 12 minutes, heat-shocked bacterial cultures, plate count assay; (2) E201, 15 minutes, heat-shocked bacterial cultures, plate count assay; (3) S101, 36 minutes, heat-shocked bacterial cultures, plate count assay; (4) S101, 24 minutes, heat-shocked bacterial cultures, light scattering assay; and (5) S101, 36 minutes, normal bacterial cultures, light scattering assay.

Figure 11A:
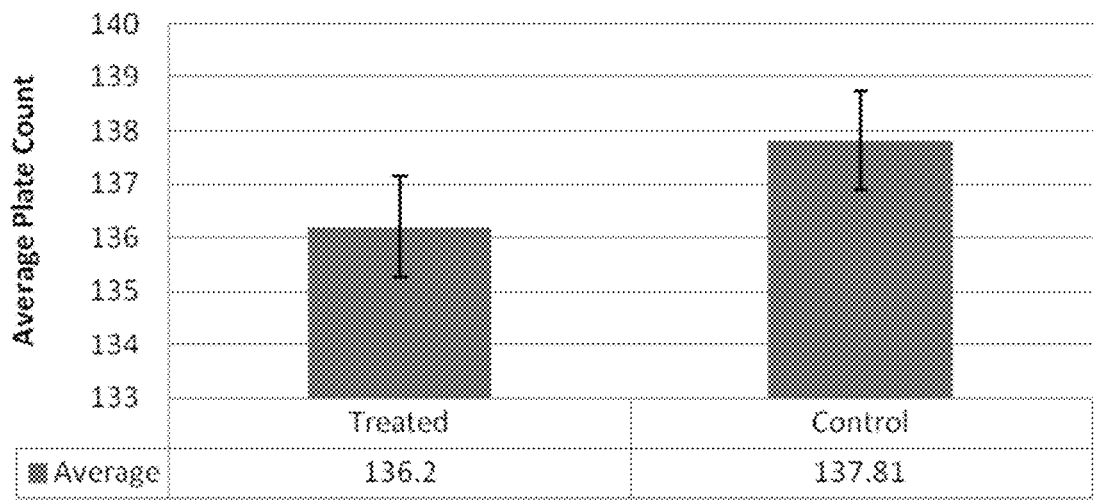
FIGS. 11a-11f show results of clinical studies performed using the subtle energy resonance regeneration system on bacterial cultures.

FIG. 11a depicts the results of Clinical study 1: S101, 12 minutes, heat-shocked bacterial cultures, plate count assay. Average plate count values are shown in FIG. 11a, and error bars indicate one standard deviation from the mean values. T-test (2-tailed, unpaired)=0.487, which means that the results of this particular clinical study show 0.3% difference, which is not a significant difference in bacterial growth between the subtle energy resonance regeneration treated and control cultures.

Figure 11B:
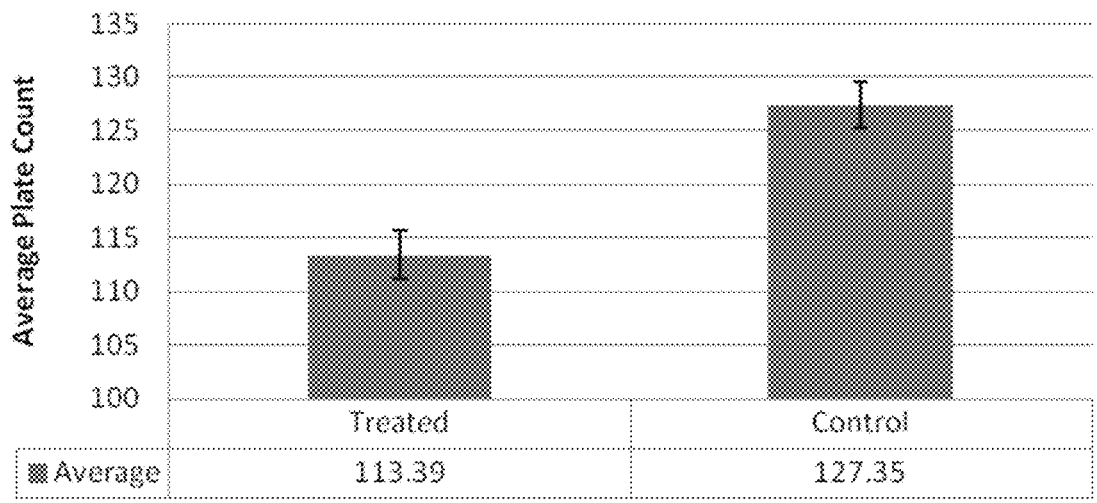

FIG. 11b shows the results of Clinical study 2: E201, 15 minutes, heat-shocked bacterial cultures, plate count assay. Average plate count values are shown in FIG. 11b, and error bars indicate one standard deviation from the mean values. T-test (2-tailed, unpaired)=3.5 E+7, meaning that p is much less than 0.0001. Thus, the results of this particular clinical study indicate a highly significant difference between the subtle energy resonance regeneration treated and control cultures. Results show that the subtle energy resonance regeneration treated cultures grow less than controls in terms of the numbers of viable bacteria. Treated bacterial cultures showed 10.9 percent less growth than controls.

Figure 11C:
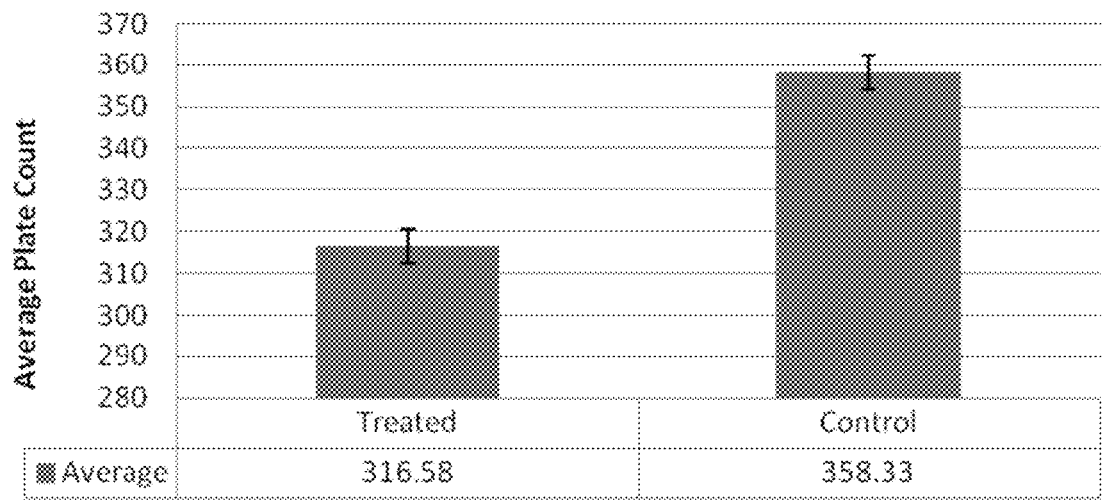

FIG. 11c illustrates the results of Clinical study 3: S101, 36 minutes, heat-shocked bacterial cultures, plate count assay. Average plate count values are shown in FIG. 11c, and error bars indicate one standard deviation from the mean values. T-test (2-tailed, unpaired)=1.72E-20, meaning that p is much less than 0.0001. Thus, the results of this particular clinical study indicate a highly significant difference between subtle energy resonance regeneration treated and control cultures. Results show that the subtle energy resonance regeneration treated cultures grow significantly less than controls in terms of the numbers of viable bacteria. Treated bacterial cultures show 11.7 percent less growth than controls.

Figure 11D:
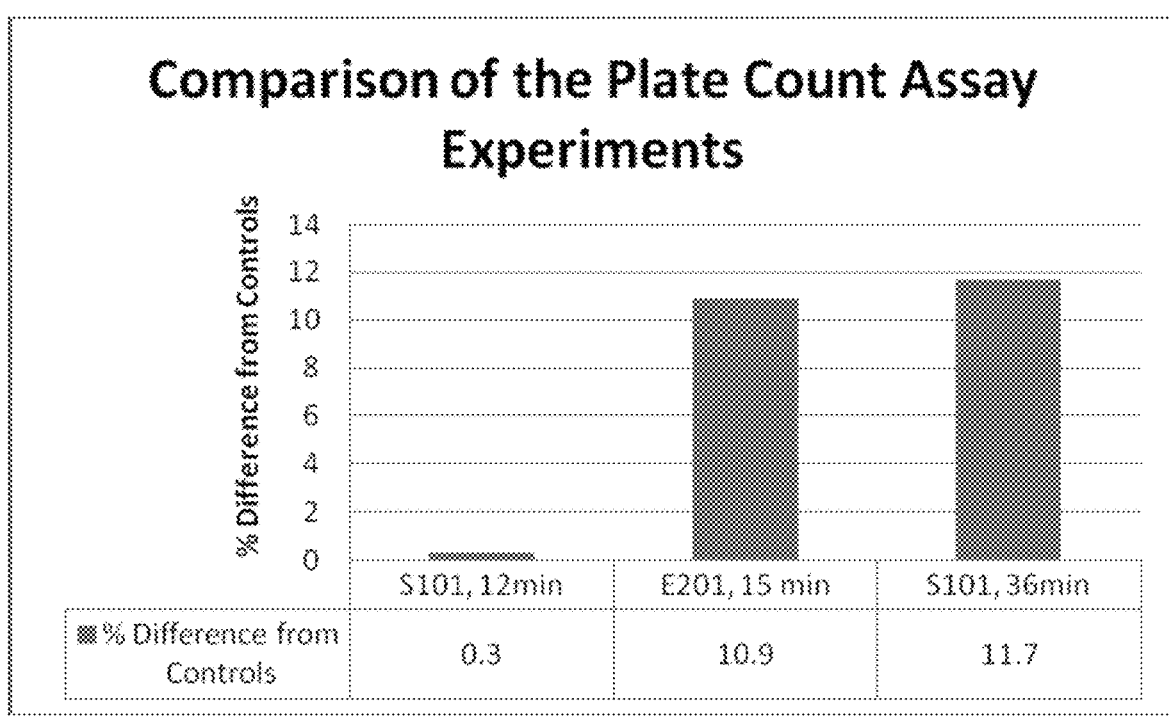

FIG. 11d depicts a comparison of the magnitude of the growth-suppressing effect on E. coli cultures for Clinical studies 1-3 using different subtle energy resonance regeneration treatments and the plate count assay, indicating the percent difference in diminished bacterial growth from the controls. The 12 minute treatment of S101 produces the smallest effect (0.3%), whereas the 15 minute treatment of E201 produces 10.9%, and the 36-minute treatment of S101 produces 11.7% change in bacterial growth. The subtle energy resonance regeneration treatments diminished bacterial growth over controls. Moreover, the longer the treatment duration, the greater the diminished effect on bacterial growth, suggesting a dose-response effect over the short term.

Figure 11E:
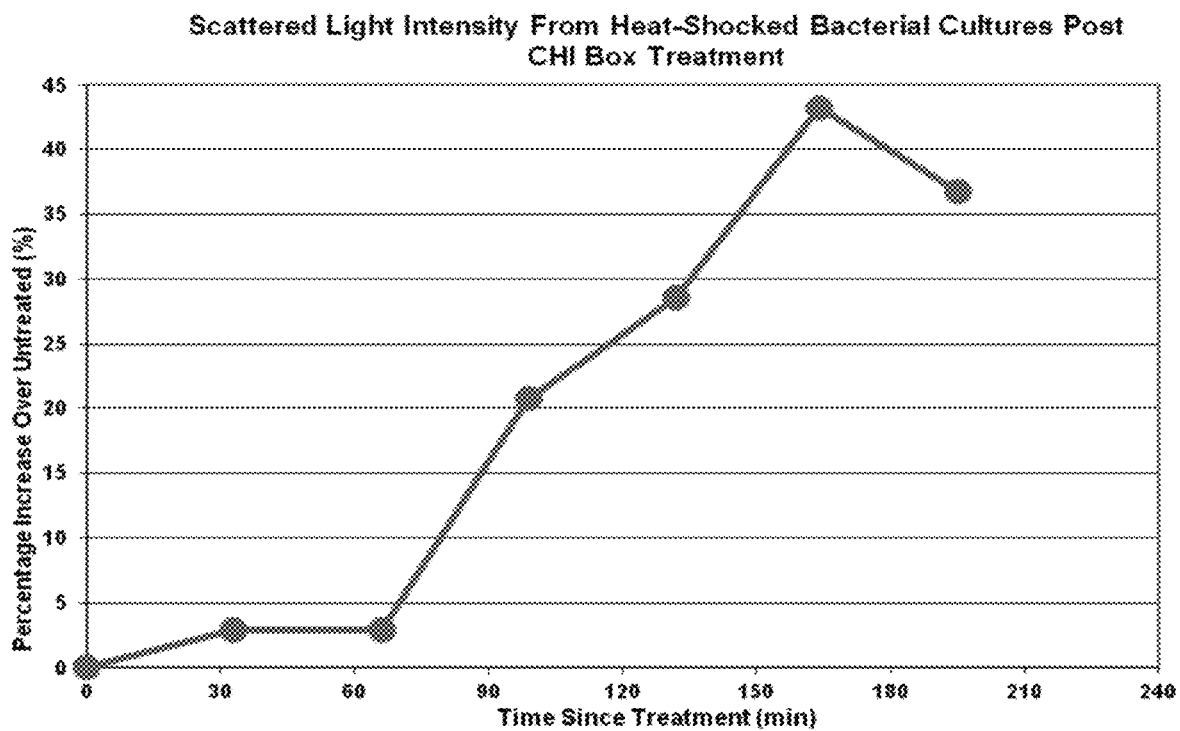

FIG. 11e shows the results of Clinical study 4: S101, 24 minutes, heat-shocked bacterial cultures, light scattering assay. FIG. 11e shows the percentage change in bacterial culture turbidity over 3+ hours as assessed by light scattering, a measure of long-term growth changes. The curve shows changes over controls, a value of 40% indicates 40% greater than controls. The curve indicates a lag in initial growth for the first hour followed by the treated cultures showing significantly increased growth over controls from 100 minutes post-treatment onward. The maximum difference between controls and treated culture samples is 43% difference at 170 min post-treatment, which is a significant difference.

Figure 11F:
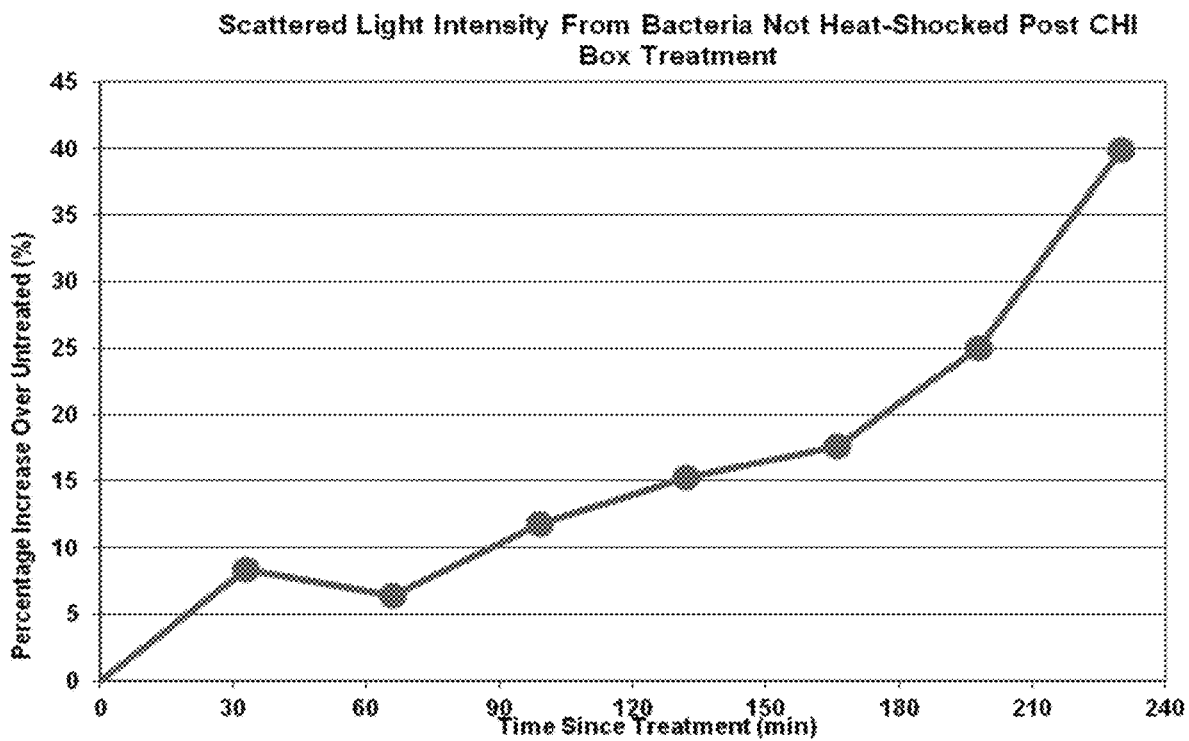

FIG. 11f illustrates the results of Clinical study 5: S101, 36 minutes, normal bacterial cultures, light scattering assay. FIG. 11f shows the percentage change in bacterial culture turbidity as assessed by light scattering over 3+ hours duration post-treatment, which is a measure of long-term growth changes. The curve shows a steady increase in growth of treated cultures over controls that is significant. A 40% difference from controls was found due to the subtle energy resonance regeneration treatment which is highly significant at 3+ hours post-treatment.

Results from the plate count assay show that heat-shocked bacteria are first diminished in viable cell count in the first hour post-treatment. However, results from light scattering clinical studies show that the treated cultures grow up to 40% more than controls at 3+ hours post-treatment. Moreover, results on healthy cultures (not heat-shocked) in light scattering clinical studies show growth stimulation by subtle energy resonance regeneration treatment is increased up to 40% over controls at 3+ hours post-treatment. Therefore, the light scattering method showed the long term growth-stimulating effects of the subtle energy resonance regeneration treatment that could not be observed by the short term plate count assay.

Short-term effects (first hour) after subtle energy resonance regeneration treatment on heat-shocked bacteria, as measured via plate count assays, showed that bacterial growth was reduced over controls. There appears to be a dose-response for this growth inhibition, in that a longer subtle energy resonance regeneration treatment reduced bacterial growth more significantly than a short-term treatment. However, long-term effects of subtle energy resonance regeneration treatment on heat-shocked bacteria, as measured via scattered light intensity over 3+ hours post-treatment showed an initial lag in growth for the first 60 minutes followed by up to 40% increased growth over controls.

Note that both FIGS. 11e, 11f show a lag time in the initial 60 minutes post-treatment, during which time the treated cultures did not differ much from the controls. For ease of comparison the graphs in both figures are plotted with the same axis scales. The lag time is especially prominent in FIG. 11e for the heat-shocked cultures, and less so for the healthy growing cultures. At longer times, the differences between controls and treated cultures are large and significant. Therefore, the light-scattering method showed long-term growth-stimulating effects of the Chi Box treatment that could not be observed by the short-term plate count assay.

The results are consistent with the conclusion that the bacterial growth response to subtle energy resonance regeneration treatment for heat-shocked cultures is biphasic, with a short-term effect of diminished growth followed by a long-term effect of enhanced growth. Following heat shock, bacteria cultures treated by subtle energy resonance regeneration signals first diminish in viable cell number up to 75 minutes, but later recover dramatically to grow much faster than controls, on the order of 40% greater growth at 3+ hours post-treatment.

It is possible that a biphasic response was observed with the subtle energy resonance regeneration treatment because the clinical studies used a high intensity to treat the bacterial cultures, which may have initially thwarted their growth and yet stimulated their recovery and growth over the long term. A biphasic response was not observed with Reiki healers or any other healers whom were previously studied using these same bacterial growth bioassays for biofield therapy. There exist, however, other instances of biphasic responses in biology, in which an applied stimulus produces inhibitory as well as stimulatory effects. This suggests that subtle energy resonance regeneration signals have an underlying differential effect on certain internal life processes. It is highly unlikely that there was a microbial contaminant in the cultures, which were handled carefully by sterile technique, and which contained a medium that exclusively supports E. coli and closely related enteric bacteria.

In the single clinical study conducted on normal bacterial cultures without heat shock, 36 minutes of subtle energy resonance regeneration treatment was found to stimulate growth over controls steadily over time, from 7% in the first 60 min to 35% over controls at 200 minutes. Therefore, it appears that the subtle energy resonance regeneration treatment steadily increases growth of normal healthy E. coli cultures (that are not heat-shocked) over controls. In this case, we observed the typical exponential bacterial growth curve, with a treatment effect of the order of 40% increased growth over controls at 3+ hours post-treatment.

Effect of Subtle Energy Resonance Regeneration on the Electrical Properties of Human DNA As described in Appendix B entitled, "Effect of Chi Box Programs on Electrical Properties of Human DNA" by Glen Rein, Ph.D., the electrical properties of the human body can be characterized in terms of its classical and non-classical behavior. Classically speaking, electrons flow linearly between two local regions of opposite charge. However, there are now experimental demonstrations that electrons also tunnel between two points. This quantum tunneling has been recently been measured in biological systems in general, and in DNA molecules in particular. In DNA, quantum tunneling occurs within the hydrogen bond, which holds the two strands together. Thus, the more hydrogen bonds in a system, the more expressed is this quantum property. More hydrogen bonds are created when separated DNA strands recombine and wind back into its intact helical structure. Previous research indicates that bio-energy emitted from a variety of different healing arts practitioners can either wind or unwind human DNA depending on their conscious intention. Thus, healers who increase rewinding are increasing the number of hydrogen bonds and thus activating DNA at the quantum level.

The quantum properties of DNA can also be measured using a technique called non-linear dielectric spectroscopy. In this technique, current-voltage measurements demonstrate discrete current spikes at specific excitation frequencies in biological systems and water. Researchers also mathematically modeled this behavior as Josephson supercurrent mediated by intrinsic coherence domains. Therefore, current-voltage measurements measure macroscopic quantum coherent behavior of biomolecules, as well as intrinsic frequency information. Thus, it has been observed experimentally that maximum current-voltage responses correlate with an increased probability of quantum tunneling.

Another experimentally observed phenomena associated with current-voltage measurements is frequency hopping/shifting where a given frequency peak will show up shifted to higher or lower frequencies upon repeat measurements. Researchers have demonstrated that the frequency hopping/shifting occurs in biomolecules, crystals and in lasers. For example, the dielectric properties of crystals show discrete peaks which shift to a higher frequency when the temperature is increased. Researchers conclude that such frequency shifts were related to frequency hopping when electrical current moves through a material (charge carrier transport). Frequency hopping is considered a quantum property of the system being measured. Due to frequency hopping, data collected in the present study was calculated as percent occurrence—how many times a measurement response occurred at a specific frequency.

Electrical measurements at a specific resonance frequency also exhibit non-local quantum behavior. Such behavior includes resonance emissions of highly coherent light, electron tunneling and resonant interactions between molecules. In light of the quantum processes associated with resonance conditions, the likelihood that such processes underlie the induced current response, measured in the present clinical studies, it is likely that the reported electrical resistance data will be a mixture of quantum and classical behavior.

In the present study, nonlinear dielectric spectroscopy was used to measure intrinsic frequencies of human DNA. DNA is stimulated with a weak electric field at varying frequencies (1 Hz to 100 kHz) and the induced current is measured. Since resonance and frequency hopping are quantum properties of DNA, it is proposed here that the non-classical energy emitted from the subtle energy resonance signals produced according to the present disclosure can best be measured in a quantum system like DNA.

In addition to measuring the dielectric properties (current-voltage responses) of DNA, a second method was used in the present study, which involves measuring the electrical conductivity of DNA. Electrical conductivity refers to the movement of electrons from a negatively charged region (of a cell or a bio-molecule) to a positively charged region. In the case of proteins, electrical current will flow along a strand from a negatively charged amino acid to a positively charged amino acid. In DNA, electrons will flow from a hydroxyl (OH—) ion to an amine (NH3+). Although electrical properties of bio-molecules correlate well with their well-established physical-chemical properties, it is only recently that scientists have begun to seriously investigate the electrical properties of bio-molecules. In general it is known that increasing electrical conductivity makes biological systems function more efficiently.

Electrical conductivity of DNA, for example, is well known to occur along its central axis and across individual strands. In the case of DNA, conductivity measures correlate with the functional activity of DNA repair. Thus, increasing conductivity is associated with increased ability of DNA to repair itself and repaired DNA has 20-fold higher conductivity than the same DNA when damaged. Increased conductivity of DNA is also associated with enhanced intrinsic self-assembly processes. On the other hand, large decreases in conductivity are associated with mismatched DNA strands.

Increased electrical conductivity (or decreased resistance) indicates that electron movement is either sped up or stronger in amplitude. In the human body, increased electrical conductivity is associated with enhanced wound-healing and DNA self-repair. In the present clinical studies, electrical conductivity refers to the ability of electrons to propagate between sending and receiving electrodes, although what was actually measured is the ability of DNA to resist that flow of electrons.

Therefore the goal is the study was to determine whether the energy emitted by any of the subtle energy resonance regeneration systems of the present disclosure can alter the dielectric properties (current-voltage response) or the electrical conductivity of human DNA. To achieve these goals the following experimental procedures were followed in two separate clinical studies. The first clinical study was done with nine different subtle energy resonance regeneration programs and the second clinical study was done on the two similar de-stress programs.

Method 1: Measuring Intrinsic Frequencies of Biomolecules

Dielectric spectroscopy is a technique involving current-voltage measurements, which generates frequency information about molecules. A modified version of dielectric spectroscopy was used in the present study where two electrodes from a potentiometer are inserted directly into the solvent and into the DNA solution. Proprietary modifications of standard dielectric spectroscopy typically include: (1) taking experimental measurements under resonance conditions; (2) calculating probabilistic occurrences of voltage spikes (not signal strength); or (3) using non-Euclidean geometry to design appropriate antenna/electrodes. When 15 sequential measurements are taken in a row, the magnitude of the induced current response at a particular frequency varies considerably.

If the induced current response is particularly strong, it can be considered coherent (laser-like). Moderate and weak current responses were also observed. When calculating the final percent occurrence values an occurrence was recorded whether it was small, medium or large in magnitude. In the present study, measurements were taken at a variety of excitation conditions by adjusting the frequency (from 10 to 100 kHz) and amplitude (from 1-20 mV) of the voltage spike. A series of 12-15 independent sequential measurements were taken for each sample. A voltage spike is generated from one electrode and the induced current signal (in nanoamperes) is recorded in the second electrode.

The data was transferred to an Excel spreadsheet for analysis. Due to a phenomenon known as frequency hopping, the amplitude (strength) of the induced current response at a given frequency cannot be measured as with normal spectroscopic techniques. Therefore, how often the induced signal appeared, percent occurrence, at each excitation frequency was measured and used to obtain the intrinsic frequencies of DNA. The percent occurrence is a measure of signal strength at each frequency (see data in FIG. 12a).

Method 2: Measuring Frequency-Specific Electrical Resistance

Electrical conductivity can be readily measured using commercial digital conductivity meters. Technically these meters measure resistance and then convert it to conductivity. Resistance to current is measured in kilohms using a fixed frequency between 1-3 kHz. This frequency range was arbitrarily chosen and is very limited.

The technique also measures electrical conductivity in terms of resistance (kilohms), but takes measurements at specific frequencies higher than 3 kHz. A specific frequency was chosen based on the intrinsic frequencies of the DNA which were predetermined using the method (1) as described in part I. All electrical resistance measurements were done using method (2) before and after exposing the DNA to the energy emitted from the subtle energy resonance regeneration system for varying amounts of time. Thirty minute exposures were optimal and used in all clinical studies.

Results

When measuring the intrinsic frequencies of DNA, the solvent (distilled water) was measured first. Then the contribution of the solvent was subtracted from the measurements of the DNA sample which also contained water, so that the intrinsic frequencies of the DNA itself could be calculated. Raw data for these calculations are not shown, but the intrinsic frequencies of 22.4, 28.2, 35.5, 42.2, 44.7, 53.1, 70.8 and 84.1 kHz were obtained.

Figure 12A:
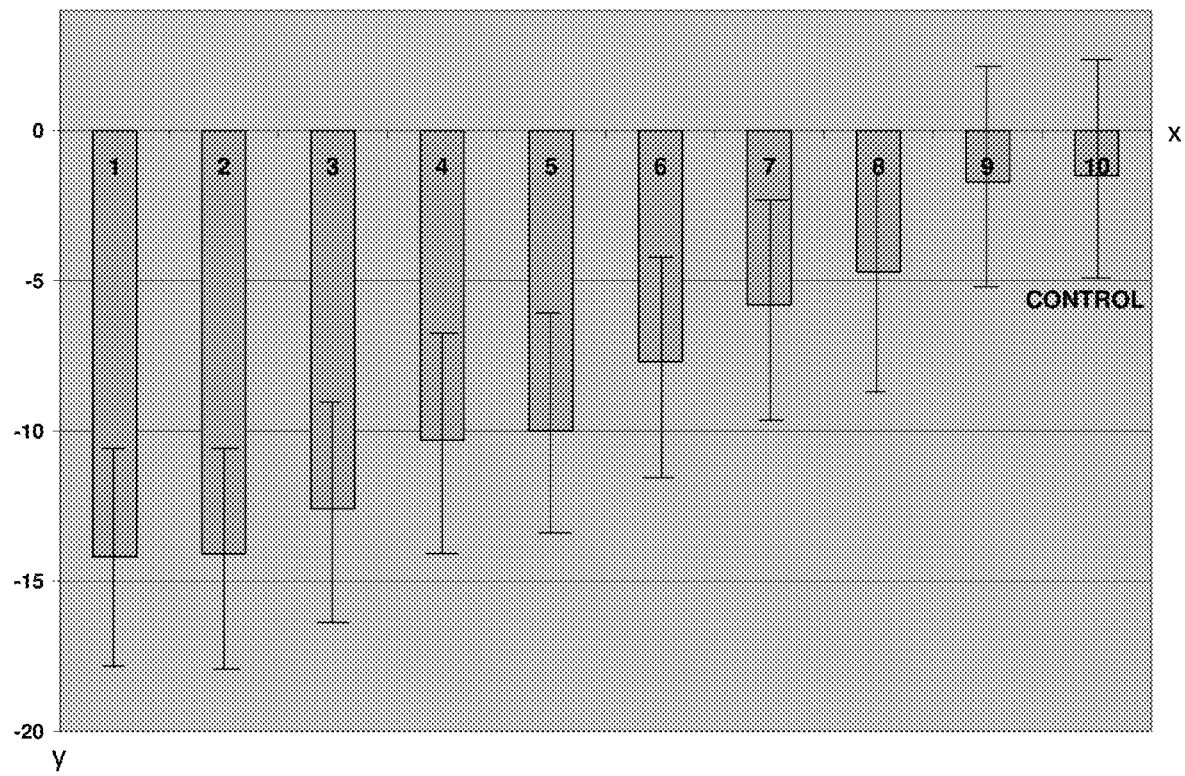
FIGS. 12a-12b show results of clinical studies recording the effect of the subtle energy resonance regeneration system on the electrical properties of human DNA.

FIG. 12a shows percent decrease in electrical resistance of DNA after treatment with various programs (measured in kilohms) with a tolerance of +/−4% of the first clinical study. Using the strongest intrinsic frequency of 22.4 kHz from above, electrical resistance was measured using method (2) in kilohms for both the solvent and the DNA. The final resistance was calculated by subtracting these two measured values. In all cases, the resistance decreased after exposure to the energy emitted by the subtle energy resonance regeneration system. The reciprocal relationship between resistance and conductivity illustrates that all subtle energy resonance regeneration programs caused an increase in conductivity.

The data in FIG. 12a was calculated as the percent decrease in resistance relative to the initial value before treatment. Percent decrease can be considered a measure of the strength of the effect. This raw data is presented in vertical axis in FIG. 12a. The numbers of the horizontal axis represent the different subtle energy resonance regeneration programs. Repeat control measures vary by 8% or less. As observed in FIG. 12a, program 6-9 overlap the range of the control when error bars are included. Therefore, five programs (1-5) where error bars do not overlap are statistically significant. This method is an alternative to using t-tests to determine statistical significance. The 5 significant programs are addictions, alleviating allergies, alleviating Lyme and both de-stress programs.

Figure 12B:
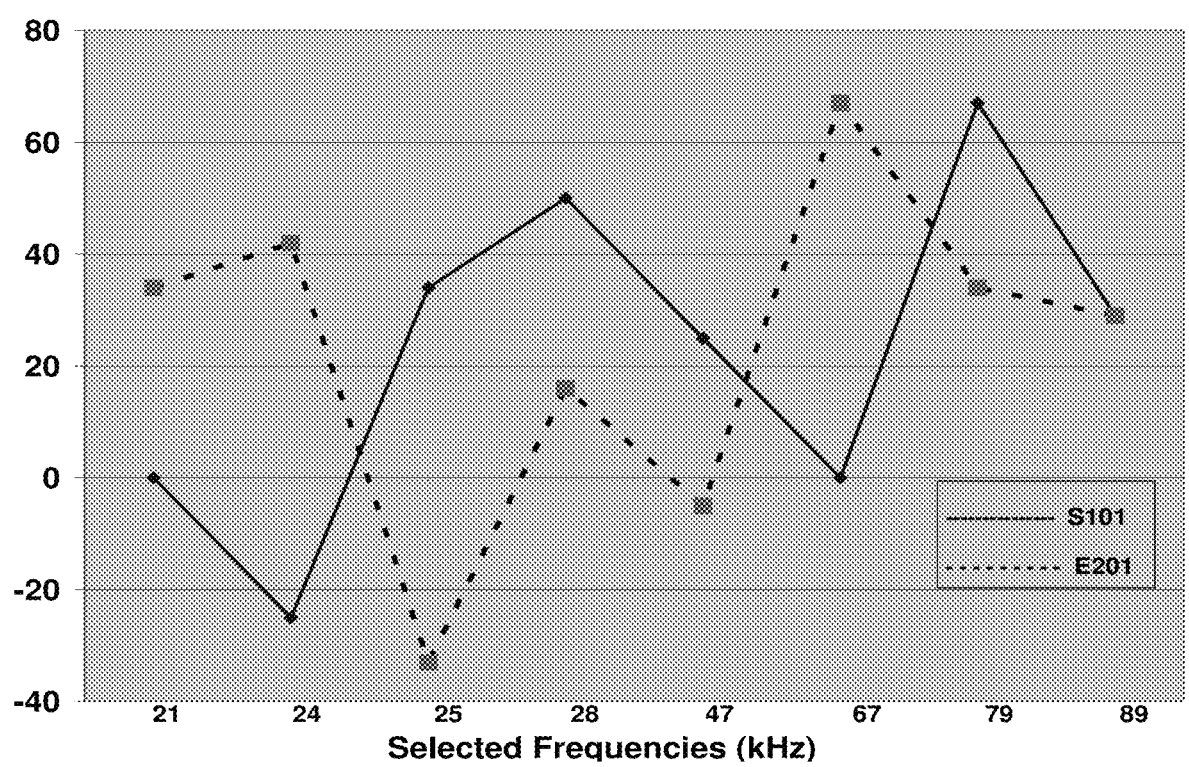

FIG. 12b shows percent change (compared to controls) for two de-stress programs at chosen DNA frequencies of the second clinical study. The data in FIG. 12b was obtained by measuring frequency information in DNA before and after treatment with two subtle energy resonance regeneration programs using method (1). The results are calculated as average percent occurrence values (strength of the signal) from twelve independent clinical studies. These selected frequencies were chosen because they occur where large differences between treated and untreated (control) DNA samples were observed and are not necessarily intrinsic frequencies of DNA as previously identified. These differences were plotted in FIG. 12b as percent change relative to controls at certain frequencies. The magnitude of these differences was as much as 3 to 4-fold indicating the sensitivity of the response.

DISCUSSION AND CONCLUSION

Measuring electrical resistance using the intrinsic frequencies of the target is a new bio-assay which allows measurement of the quantum properties of DNA. The increased sensitivity of the assay allows discrimination between the different programs stored in the subtle energy resonance regeneration system of the present disclosure. Pain-killer (addiction) and allergies were the most effective at decreasing the electrical resistance of human DNA in vitro (see FIG. 12a). In addition, both de-stress programs and the Lyme program also showed large decreases. In all five of these programs a statistically significant effect was observed. The magnitude of this effect was 14%, which is similar to that observed in previous clinical studies when other healers treated DNA directly and conformational changes or frequency changes.

The liver detox program on the other hand did not decrease DNA resistance. Programs that have a weak effect on DNA will likely have other beneficial healing effects on the body mediated by other mechanisms which are not DNA-dependent.

The second part of this study, method (1) was used to measure the effects of the two de-stress programs in detail. The two de-stress programs were chosen because they were also being evaluated in a separate study in a different lab where the two de-stress programs were both effective at stimulating bacteria growth. The data in FIG. 12a compares the same intention (to de-stress) held by two different practitioners. Although these two programs could not be distinguished by electrical resistance measures, the intrinsic frequency method did reveal differences. At certain frequencies, the strength of the signal (percent occurrence) response was different. At some frequencies the S101 program produced a large effect, but the E201 program did not. At other frequencies the E201 program produced a large effect, but the S101 signal did not. Only at 79 and 89 kHz did both programs have a similar stimulatory effect, although the effect at 89 kHz was somewhat weaker. Both programs activate five intrinsic frequencies, although the signal strength at each frequency is different. This pattern information can be used in future studies to distinguish other subtle energy resonance regeneration programs.

The method (2) measures the electrical properties using an intrinsic frequency of the specific bio-molecule of interest. Intrinsic frequencies of DNA were pre-determined using a separate technique of method (1). The technique is a modification of dielectric spectroscopy for measuring electrical changes at specific frequencies. Using the strongest measured intrinsic frequency of DNA (22.4 kHz), electrical resistance of DNA was then determined, using method (2) before and after exposure to 9 different programs in the subtle energy resonance regeneration system of the present disclosure. All programs decreased the electrical resistance of DNA except the liver program. The addiction/pain killers program and the allergy program were the most effective. The maximum effect observed showed a 14% decrease compared to controls which is similar to previous clinical studies by the author using other healers who treated the DNA directly.

A second set of clinical studies measured changes in DNA's own intrinsic frequencies in response to the two de-stress programs using method (1). Signal strength at certain frequencies showed a 3 to 4-fold increase compared to untreated controls. The method could distinguish between these two similar programs where resistance measures could not. The two methods show that the subtle energy resonance regeneration system radiates an energy which changes the electrical properties of human DNA.

It is to be understood that one or more embodiments of the present disclosure include the recording of specific resonant frequencies of trees, plants, flowers, humans, other biological subjects, treated water, and various types of suitable crystals.

Figure 13:
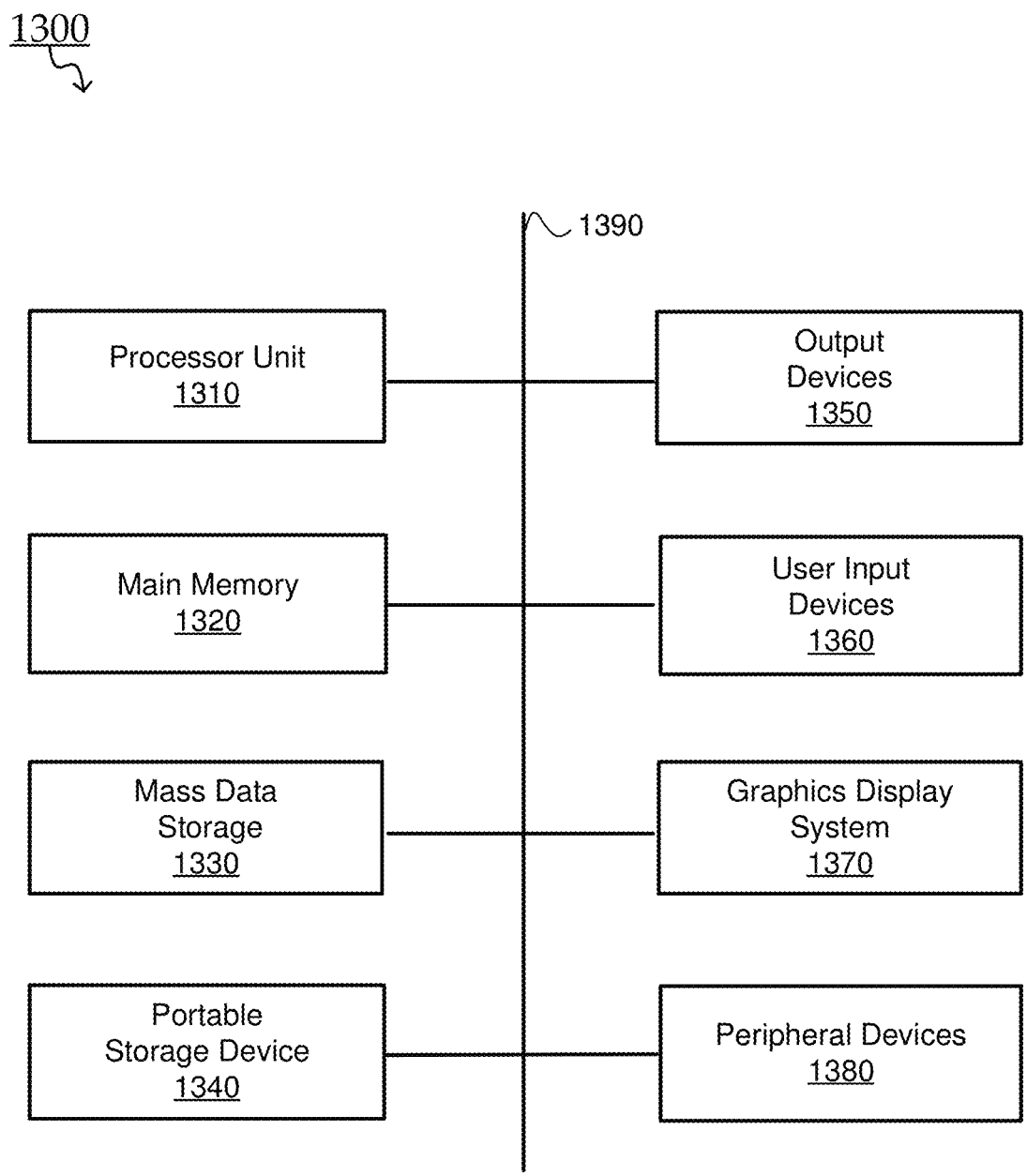
FIG. 13 is a block diagram of an example computer system that may be used to implement embodiments of the present disclosure.

FIG. 13 illustrates an exemplary computer system 1300, which may be 170 or 480, that may be used to implement some embodiments of the present disclosure. The computer system 1300 of FIG. 13 may be implemented in the contexts of the likes of computing systems, networks, servers, or combinations thereof. The computer system 1300 of FIG. 13 includes one or more processor unit(s) 1310 and main memory 1320. Main memory 1320 stores, in part, instructions and data for execution by processor unit(s) 1310. Main memory 1320 stores the executable code when in operation, in this example. The computer system 1300 of FIG. 13 further includes a mass data storage 1330, portable storage device 1340, output devices 1350, user input devices 1360, a graphics display system 1370, and peripheral devices 1380.

The components shown in FIG. 13 are depicted as being connected via a single bus 1390. The components may be connected through one or more data transport means. Processor unit(s) 1310 and main memory 1320 are connected via a local microprocessor bus, and the mass data storage 1330, peripheral device(s) 1380, portable storage device 1340, and graphics display system 1370 are connected via one or more input/output (I/O) buses 1390.

Mass data storage 1330, which can be implemented with a magnetic disk drive, solid state drive, or an optical disk drive, is a non-volatile storage device for storing data and instructions for use by processor unit(s) 1310. Mass data storage 1330 stores the system software for implementing embodiments of the present disclosure for purposes of loading that software into main memory 1320.

Portable storage device 1340 operates in conjunction with a portable non-volatile storage medium, such as a flash drive, floppy disk, compact disk, digital video disc, or USB storage device, to input and output data and code to and from the computer system 1300 of FIG. 13. The system software for implementing embodiments of the present disclosure is stored on such a portable medium and input to the computer system 1300 via the portable storage device 1340.

User input devices 1360 can provide a portion of a user interface. User input devices 1360 may include one or more microphones, an alphanumeric keypad, such as a keyboard, for inputting alphanumeric and other information, or a pointing device, such as a mouse, a trackball, stylus, or cursor direction keys. User input devices 1360 can also include a touchscreen. Additionally, the computer system 1300 as shown in FIG. 13 includes output devices 1350. Suitable output devices 1350 include speakers, printers, network interfaces, and monitors.

Graphics display system 1370 includes a liquid crystal display (LCD) or other suitable display device. Graphics display system 1370 is configurable to receive textual and graphical information and processes the information for output to the display device.

Peripheral devices 1380 may include any type of computer support device to add additional functionality to the computer system 1300.

The components provided in the computer system 1300 of FIG. 13 are those typically found in computer systems that may be suitable for use with embodiments of the present disclosure and are intended to represent a broad category of such computer components that are well known in the art. Thus, the computer system 1300 of FIG. 13 can be a personal computer (PC), handheld computer system, telephone, mobile computer system, workstation, tablet, phablet, mobile phone, server, minicomputer, mainframe computer, wearable, or any other computer system. The computer may also include different bus configurations, networked platforms, multi-processor platforms, and the like. Various operating systems may be used, including UNIX, LINUX, WINDOWS, MAC OS, PALM OS, QNX ANDROID, IOS, CHROME, TIZEN and other suitable operating systems.

Transmission media may include coaxial cables, copper wire, gold wire, and fiber optics including various computer busses. Transmission media can also take the form of acoustic, magnetic, electromagnetic, or light waves such as those generated during radio frequency (RF) and infrared (IR) data communication. Carrier wave or other media for transmission of information signals may also be used. Various forms of transmission media may be involved in carrying one or more signals, singly or in combination, to a target subject for subtle energy resonance.

Such receiving and regeneration subtle energy resonance systems as described in the disclosed embodiments have been shown to have beneficial results in resolving, modifying, reducing, changing, and ameliorating biological conditions in target subjects of various types including cellular organisms to human organisms.

The use of the present disclosure with long term storage of subtle energy resonance signals has opened a new field of study that promises to impact the integrative health profession. Tuning, filtering, amplitude adjustment, or any other signal enhancement of the recorded subtle energy resonance signal are utilized for manipulation of cell resonance during regeneration transmission, and are contained within the scope of the present disclosure. Embodiments of the present disclosure may also be used for research to provide a desired resonance in a subject. In addition, EM Faraday cage shields of the present disclosure may provide isolation chambers to test various commercial products that emit EMF interference or AC noise.

While the present disclosure has been described in connection with a series of preferred embodiments, these descriptions have been presented by way of example only and are not intended to limit the scope of the appended claims to a particular form set forth herein. Thus, the breadth and scope of a preferred embodiment should not be limited to any of the above-described exemplary embodiments. To the contrary, the present descriptions are intended only to cover such alternatives, modifications, and equivalents as may be included within the scope and spirit of the present disclosure as defined by any appended claims and otherwise appreciated by one of ordinary skill in the art. The scope of the present disclosure should, therefore, be determined not with reference to the above description, but instead should be determined with reference to the full scope of equivalents.

What is claimed is:

1. A system for capturing and recording subtle energy resonance, comprising:
    a) an electromagnetic shield;
    b) an antenna array disposed within the electromagnetic shield, the antenna array having at least one receiving antenna operable to capture subtle energy resonance signals, each receiving antenna comprising:
        i) a housing;
        ii) a sensor plate cover, coupled to the housing, that receives at least one subtle energy resonance signal from a source; and
        iii) an amplifier circuit board coupled to a conductive disk; and
    c) a multi-channel signal processor coupled to each receiving antenna of the antenna array, the multi-channel signal processor converting the at least one subtle energy resonance signal into at least one digital subtle energy resonance signal, and storing the at least one digital subtle energy resonance signal into a memory.

2. The system as recited in claim 1, wherein the electromagnetic shield includes a plurality of isolated and insulated layers.

3. The system as recited in claim 2, wherein the plurality of isolated and insulated layers includes an inner layer isolated from ground and a grounded outer layer.

4. The system as recited in claim 1, wherein the amplifier circuit board is coupled to the sensor plate cover via a contact lead, the amplifier circuit board being a signal conditioning Field-Effect Transistor receiver circuit board.

5. The system as recited in claim 1, further comprising a first and a second microphone, the first microphone disposed within the electromagnetic shield and the second microphone disposed outside of the electromagnetic shield, the first and the second microphone communicatively coupled to a second signal processor.

6. The system as recited in claim 1, wherein the multi-channel signal processor includes an analog-to-digital converter that samples at a sampling frequency of at least 192 kHz at 24-bit.

7. A system for regeneration of subtle energy resonance, comprising:
    a memory having stored at least one digital subtle energy resonance signal;
    a signal processor communicatively coupled to the memory, the signal processor having a digital-to-analog converter that converts the at least one stored digital subtle energy resonance signal into at least one analog subtle energy resonance signal, wherein a first and a second output channel of the signal processor are coupled to a first amplifier; and
    at least one regeneration antenna electrically coupled to the signal processor, wherein the first amplifier is configured to amplify the at least one analog subtle energy resonance signal prior to transmitting the amplified at least one analog subtle energy resonance signal to a first and a second regeneration antenna of the at least one regeneration antenna, each of the first and second regeneration antennas including at least one of a spiral coil having a plurality of loops and a scalar antenna, such that each regeneration antenna is configured to regenerate the at least one analog subtle energy resonance signal.

8. The system as recited in claim 7, wherein a third and a fourth output channel of the signal processor are coupled to a second amplifier, the second amplifier amplifying the at least one analog subtle energy resonance signal prior to transmitting the amplified at least one analog subtle energy resonance signal to a third and a fourth regeneration antenna of the at least one regeneration antenna.

9. The system as recited in claim 8, wherein the first and the second amplifiers are dual channel Field Effect Transistor amplifiers.

10. The system as recited in claim 7, wherein each loop of the plurality of loops comprises a predetermined ratio between a predetermined height and a predetermined width of each loop.

11. The system as recited in claim 7, further comprising a digital regeneration device having the memory and the signal processor, the digital regeneration device being portable.

12. The system as recited in claim 11, wherein the digital regeneration device is coupled to the at least one regeneration antenna via a 3.5 mm socket.

13. The system as recited in claim 11, wherein the spiral coil of the at least one regeneration antenna is disposed on a printed circuit board coupled to the digital regeneration device.

14. The system as recited in claim 7, wherein the at least one analog subtle energy resonance signal is a 24-bit, 192 kHz signal.

15. A method for capturing and recording subtle energy resonance signals, comprising:
    capturing, via an antenna array from a source, at least one subtle energy resonance signal, the antenna array comprising: a housing, a conductive disk, and a first amplifier, wherein the antenna array and the source are disposed within an electromagnetic shield;
    amplifying, via the first amplifier, the at least one subtle energy resonance signal;
    receiving, via a first microphone within the electromagnetic shield, a first reference acoustic signal from the source;
    receiving, via a second microphone outside the electromagnetic shield, a second reference acoustic signal;
    converting, via a first signal processor, the at least one subtle energy resonance signal into at least one digital subtle energy resonance signal;
    transmitting, via the first signal processor, the at least one digital subtle energy resonance signal to a computing device having one or more processors and a memory; and
    storing, via the one or more processors, the at least one digital subtle energy resonance signal into the memory.

16. The method as recited in claim 15, further comprising: determining a time signature from the first and the second reference acoustic signals.

17. The method as recited in claim 15, further comprising: analyzing an amplitude and at least one frequency of the at least one digital subtle energy resonance signal; and standardizing an input power level of the at least one subtle energy resonance signal based on the analysis.

18. The method as recited in claim 15, wherein the converting the at least one subtle energy resonance signal includes sampling at a sampling frequency of at least 192 kHz at 24-bit.

19. A method for regeneration of subtle energy resonance, comprising:
- receiving, via one or more processors, at least one digital subtle energy resonance signal from a memory;
- converting, via a signal processor communicatively coupled to the memory, the at least one digital subtle energy resonance signal into at least one analog subtle energy resonance signal;
- amplifying, via an amplifier, the at least one analog subtle energy resonance signal, the amplifier being communicatively coupled to the signal processor and at least one regeneration antenna, wherein each regeneration antenna of the at least one regeneration antenna includes a spiral coil having a plurality of loops, and each loop of the plurality of loops comprises a predetermined ratio between a predetermined height and a predetermined width of each loop; and
- outputting and transmitting the at least one analog subtle energy resonance signal via the at least one regeneration antenna.

20. The method as recited in claim 19, wherein each regeneration antenna is configured to regenerate the at least one analog subtle energy resonance signal.

21. The method as recited in claim 20, wherein transmitting the at least one analog subtle energy resonance signal includes disposing the at least one regeneration antenna a predetermined distance away from a subject receiving the at least one regenerated analog subtle energy resonance signal.

22. The method as recited in claim 19, wherein the at least one regeneration antenna is a scalar antenna.

* * * * *